(12) United States Patent
Kuypers et al.

(10) Patent No.: US 8,304,245 B2
(45) Date of Patent: Nov. 6, 2012

(54) MICROFLUIDIC FLOW LYSOMETER DEVICE, SYSTEM AND METHOD

(75) Inventors: Franciscus Albertus Kuypers, El Cerritos, CA (US); Won Chul Lee, Berkeley, CA (US); Albert P. Pisano, Danville, CA (US)

(73) Assignee: Children's Hospital and Research Center at Oakland, Oakland, CA (US)

( * ) Notice: Subject to any disclaimer, the term of this patent is extended or adjusted under 35 U.S.C. 154(b) by 685 days.

(21) Appl. No.: 11/934,718

(22) Filed: Nov. 2, 2007

(65) Prior Publication Data

US 2009/0117555 A1    May 7, 2009

(51) Int. Cl.
 C12Q 1/34 (2006.01)
 C12Q 1/68 (2006.01)
 C12Q 1/00 (2006.01)
 C12M 1/34 (2006.01)
 C12M 1/00 (2006.01)

(52) U.S. Cl. ......... 436/63; 435/6.1; 435/4; 435/34; 435/288.7; 435/283.1

(58) Field of Classification Search .......... 436/63; 435/4, 6, 29, 34, 283.1, 287.1, 288.7
See application file for complete search history.

(56) References Cited

U.S. PATENT DOCUMENTS

| | | |
|---|---|---|
| 6,586,253 B1 | 7/2003 | Harrison et al. |
| 6,783,647 B2 | 8/2004 | Culbertson et al. |
| 6,949,343 B2 | 9/2005 | Coull |
| 6,970,245 B2 * | 11/2005 | Fritz et al. ............ 356/400 |
| 7,176,018 B2 | 2/2007 | Tai |
| 2004/0058423 A1 * | 3/2004 | Albritton et al. ...... 435/173.7 |

OTHER PUBLICATIONS

U.S. Appl. No. 10/429,282, filed May 2, 2003, Albritton.
Gawad et. al., "Micromachined impedance spectroscopy flow cytometer for cell analysis and particle sizing", Lab on a Chip, 2001, 1, 76-82.
Han et. al. "Fast Electrical Lysis of Cells for Capillary Electrophoresis", Anal. Chem. 2003, 75, 3688-3696.
Krylov et. al., "Instrumentation for Chemical Cytometry", Anal. Chem. 2000, 72, 872-877.
McClain, "Single cell lysis on microfluidic devices", Proceedings of the uTAS 2001 Symposium—ornl.gov.
Wolf et. al., "Integrating advanced functionality in a microfabricated high-throughput fluorescent-activated cell sorter", Lab Chip, 2003, 3, 22-27.

(Continued)

*Primary Examiner* — Christine T Mui
(74) *Attorney, Agent, or Firm* — David R. Stevens; Stevens Law Group

(57) ABSTRACT

The invention provides a device, system and method that enables a microfluidic flow lysometer cell analyzer. Using a population of suspended living cells, cell surface molecule detection reagents, and cell cytoplasm (or nuclear) molecule detection reagents, this microfluidic cell analyzer can rapidly analyze a population of cells by running them on a one-at-a-time basis through small capillary channels. The cell's morphology or surface markers are analyzed, then the cells are lysed, and the molecules present in the cell's cytoplasm or nuclear material are analyzed. Cell morphology is then analyzed as the cell surface molecules are correlated with the molecules present in the same cell's cytoplasm or nucleic acids, and this correlated cell population data is then presented to a user for interpretation. The invention also addresses issues such as device fouling, correction for experimental artifacts (incomplete cell lyis, variable cell debris volume effects), and inadequate data collection that hampered earlier efforts in this area.

25 Claims, 12 Drawing Sheets

OTHER PUBLICATIONS

Niewenhuis et. al., "Integrated flow-cells for novel adjustable sheath flows", Lab Chip, 2003, 3, 56-61.

Munson et. al, "Suppression of non-specific adsorption using sheath flow" Lab Chip 2004, 4, 438-445.

Zhang et. al. "Creating new fluorescent probes for cell biology", Nature Reviews, Molecular and Cell Biology, vol. 3, p. 906-918, Dec. 2002.

Cai et. al, "Ultra-Low-Volume, Real-Time Measurements of Lactate from the Single Heart Cell Using Microsystems Technology", Anal. Chem. 2002, 74, 908-914.

* cited by examiner

MICROFLUIDIC FLOW LYSOMETER DEVICE, SYSTEM AND METHOD

BACKGROUND

The invention relates to methods and devices to rapidly correlate individual cell morphology and cell surface characteristics with the same individual cell's cytoplasm or nuclear biochemical constituents, and to perform this analysis over an entire cell population.

Living cells are extremely complex entities that represent the fundamental building blocks of higher forms of life. Accordingly, there is great interest in observing and analyzing cells. Many methods and related devices exist that allow researchers to perform experiments on cells, both living and dead, and to observe such cells, but given the complexity of the problem, further advances are desirable.

All eukaryotic cells (with the exception of red calls and platelets) contain a nucleus (which contains the bulk of the cell's genetic material) surrounded by cytoplasm. In the cytoplasm, enzymes and RNA, controlled by the cell's genetic material, conduct thousands of specialized biochemical reactions. Some of these biochemical reactions are common to all cells, but others are unique to the particular cell type in question. The cell cytoplasm is in turn covered by a cell membrane, which itself is usually quite complex. Typically, cell membranes consist of hundreds or thousands of different types of membrane proteins and specialized lipids, embedded in a fluid two-dimensional lipid bilayer. Just as the cytoplasm has different biochemical pathways that differ according to cell type and function, so the cell membrane has different membrane proteins and lipids that also differ according to the cell type and function.

The composition of the cell's various membrane receptor and transporter molecules, and the biochemical pathways and constituents in the cell's cytoplasm, usually control the cell's morphology (size, shape, and structure as seen under a microscope). As one example, red cell cytoplasm contains various biochemical pathways to produce adenosine triphosphate (ATP). This cytoplasmic ATP, in turn, provides power to the red cell's cytoskeletal membrane components and ion transport molecules, which these membrane components use to maintain the red cell's shape and size.

As red cells age or become damaged, their ATP levels usually drop, and the red cell's morphology (shape and size changes). Thus a correlation often exists between a red cell's particular cell surface morphology and its cytoplasmic ATP levels.

As a second example, immune system B-cells, which produce antibodies, typically have both B-cell specific antigen detecting receptor molecules on their cell surfaces, and B-cell specific biochemical pathways (some of which act to produce antibodies) going on in the cytoplasm. B-cell specific genes that are activated in the B-cell nucleus in turn control these B-cell specific membrane components and cytoplasmic biochemical pathways.

Similarly, immune system T cells, which don't produce antibodies, but which play an active role in immune system regulation, as well as detecting and destroying pathogens, have a different set of membrane receptors, different cytoplasmic biochemical pathways and components, and different genes that are activated in the nucleus. It is likely that each of the many thousands or millions of different cell types in the body has its own unique pattern of morphology, membrane molecules, cytoplasmic molecular pathways, and nuclear genetic activation states.

Many of the advances in modern medicine and pharmacology rest upon fundamental research that has studied correlations between the cell morphology, membrane molecules, cytoplasmic molecules, and the genetic activation pathways that exist between cell populations. As a result, there is much interest in analytical technology that can enable researchers to better understand these correlations.

Although there have been many advances in analytical technology in these areas in recent years, there is room for further improvement. At present, available analytical technology primarily allows researchers to largely study isolated parts of these various systems, rather than see all the interactions between these systems as they operate across entire cell populations.

As an example, microscopy methods allow researchers to study cell morphology. Cytological stains allow researchers to draw some inferences between, for example, cell morphology and cell membrane receptors, but the bulk of the present microscopy methods primarily work with dead and chemically processed cells, rather than living cell populations, and thus are prone to artifacts and distortion.

Biochemical methods allow researchers to grind up large numbers of cells, and study the biochemical pathways inside the large number of cells, but this process generally requires large amounts of material. As a result, traditional biochemical analysis tends to miss (average out) cell-to-cell differences, and is also prone to distortion because the greater the time interval is between disrupting the cell and analyzing the cell's cytoplasmic biochemical pathways, the greater the chance is that these pathways will become damaged or distorted.

Recently, cell-sorting techniques have become popular. Cell sorting techniques allow researchers to correlate cell morphology with various types of cell membrane molecules on a population basis, using intact living cells. These methods, exemplified by fluorescence-activated cell sorting (FACS) techniques, have greatly facilitated modern medicine, particularly in the field of cellular immunology.

Although FACS techniques represent a big step forward in allowing researchers to understand cellular properties on a population basis, these methods still do not allow researchers and clinicians to easily monitor the correlations that exist between the cell's morphology, the cell's surface molecules, and the complex biochemical pathways that occur inside of the cytoplasm or nucleus of these cells.

Earlier researchers realized that it would be desirable to produce devices that can, on a cell population basis, correlate individual cell morphology and surface characteristics with the cell's internal biochemistry. However, in spite of the long felt need for this type of device, no such device has yet been commercialized. This appears to be because prior art in this area did not perform well enough to produce robust and capable devices that would actually perform well in the hands of users, on a routine basis.

Prior art methods include U.S. Pat. No. 6,586,253 B1 to Harrison et. al.; U.S. Pat. No. 6,783,657 to Culberson et. al., US patent application 20040058423 to Albritton; and other methods.

Harrison teaches a microchip method for detecting cell contents, in which a cell is put into a fluid filled channel in a microchip, and diverted to a cell lytic region. There, the cells are lysed, and the cell contents are then analyzed at a detection zone, usually by fluorescence or luminescence detection means. Harrison's methods have not been commercialized, however, possibly because the invention did not teach any means to prevent cells or cell debris from fouling the apparatus in operation. Additionally Harrison failed to teach ways in which the analyzer might sort or screen particular cell populations prior to analysis, ways to correlate cell surface markers with cellular contents, or ways to correct the assay for distortions caused by inadequate lysis or variations in the volume of the cytoplasmic debris field of the lysed cells.

Culbertson teaches an alternate microfluidic cell analysis system. Similar to Harrison, Culberson introduces cells into a microfluidic chamber, and also utilizes electrical cell lytic techniques. However Culberson does not incorporate any cell morphology or cell surface analytical means in his device, and does not disclose means by which cell morphology or cell surface characteristics may be correlated with internal cell biochemical molecules. Like Harrison, Culberson also remains silent on methods to prevent his apparatus from becoming fouled by cells and cell debris.

Albritton teaches a "single-cell at a time" type method in which cells are lysed in a larger cell collection chamber, and the cell contents are immediately sucked into analytical capillary electrophoresis tubes. There, the cells are mixed with suitable reagents for analyzing the cytoplasm, and subjected to capillary electrophoresis. Although this method allows for very precise determination of certain cell contents, the methods are single cell based, rather than population based, and are generally unsuited for the high volume cell analysis methods contemplated by the invention.

In order to produce practical devices that can actually be used on a routine basis to solve research and clinical problems, issues such as cell pre-screening, device fouling, correction for dilution effects, correction for analytical artifacts, reasonable throughput, and adequate analytical capability need to be addressed. Here prior art has been silent.

Ideally, what is needed is some sort of rapid cell sorting or analysis device that can analyze a large population of cells (for example, the population of lymphocytes from a blood sample), and provide clinicians with accurate and timely cell population data that correlates the cell morphology (that is cell size, shape, or visual characteristics) and cell surface molecules on the surface of the various cells in this cell population with the biochemical and genetic pathways ongoing in the various cell's cytoplasm and nuclei. A device and method that would be capable of doing this correlation on an individual cell basis, and that would be capable of analyzing an entire cell population in this manner, would achieve commercial success, and would likely make many contributions to medical research as well. As will be seen, the invention provides such a device and method in an elegant manner.

DETAILED DESCRIPTION

Figure 1:
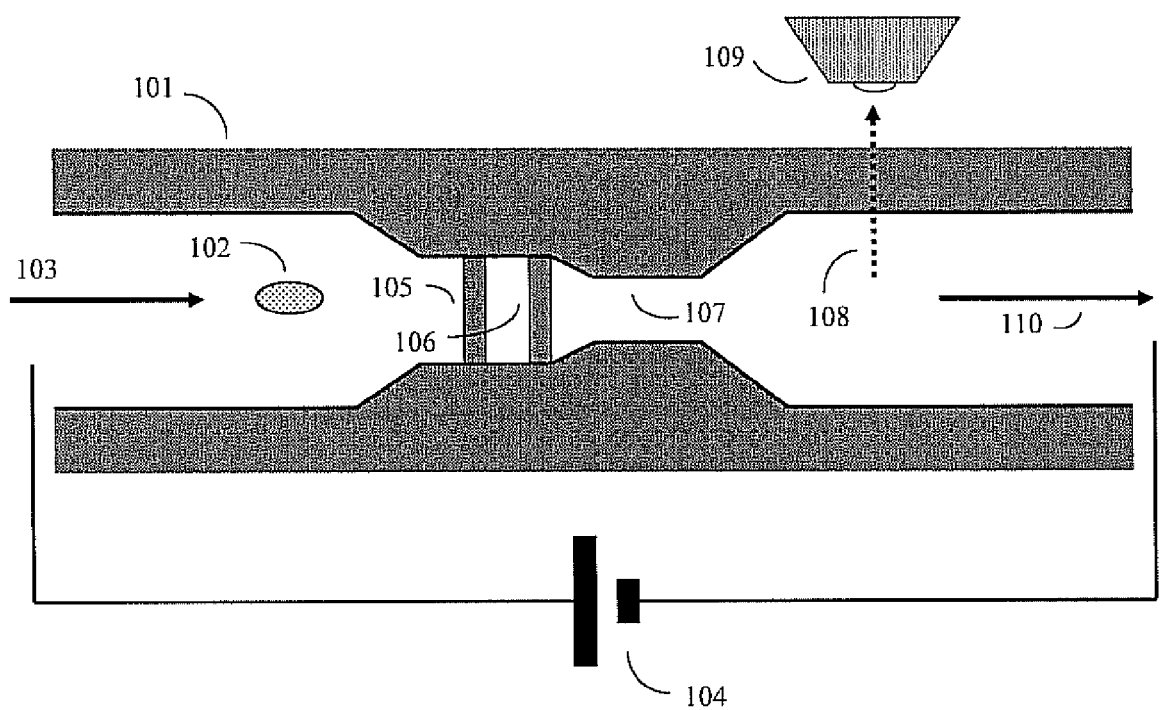
FIG. 1 shows a diagram of one embodiment of the invention.

The invention is directed to an advanced type of microfluidic cell analyzer. This microfluidic cell analyzer can rapidly analyze a population of cells by running them on a one-at-a-time (one cell at a time) basis through small capillary fluid filled channels. The device first analyzes the cell morphology or surface molecules, and then lyses the cells, and biochemically analyzes molecules of interest in the released cell cytoplasm or nuclear contents. Because the device does so in a continuous or nearly continuous flow manner, it will occasionally be referred to throughout this specification as a "flow lysometer".

As described herein, different embodiments and configurations are possible in devices, systems and methods embodying the invention. The embodiments described here, are only intended as examples, and are not intended as limitations on the spirit and scope of the invention. This includes any type of means to accomplish certain functions that pertain to the invention. Furthermore, to the extent that any means plus function language is used in the claims, they are not limited to embodiments described herein, but contemplate and include any and all types components, devices, systems and method steps known or are to be developed in the future by those skilled in the art. And, those skilled in the art will understand that different configurations are possible without departing from the spirit and scope of the invention, which is defined by the appended claims, future claims submitted during prosecution in this and related applications, and equivalents of such claims.

According to the invention, a device or system so configured can rapidly correlate cell morphology and cell surface markers with the state of the same cell's cytoplasm or nucleic acids, and presents this correlated cell population statistics data to the user in an easy-to-interpret manner. Additionally, a device or system configured according to the invention is designed to address issues such as cell pre-screening, device fouling, correction for experimental artifacts (incomplete cell lysis, variable cell debris volume dilution effects), and adequate analytical capability, that have plagued earlier efforts in this field.

The invention generally provides a continuous flow microcapillary device "flow lysometer" suitable for monitoring a cell population comprised of multiple living cells. The device contains a device and method Figure configured to observe the size or morphology or cell surface markers of intact living cells, to lyse the cells while they traverse the device, and to analyze the cytoplasm or nuclear contents of the lysed cells for biochemical markers of interest before the cytoplasm leaves the device. Optionally, the invention provides a method and device for computationally analyzing the results from the cell size, morphology, or surface markers and correlating these values with results from the cell cytoplasm or nuclear biochemical markers.

In one embodiment, the invention provides a method for performing a population analysis on a plurality of living cells while in transit in at least one dynamic microfluidic pathway, where a population of living cells having cell indicia is analyzed. The population of cells is first transmitted through the device, and the cell indicia are analyzed. Next, at least one cell is lysed while transiting through a microfluidic pathway, producing cell debris. This debris is then analyzed, so that at least one lysed cell can be analyzed for debris indicia present in the cell debris. According to the invention, it is now possible to analyze a single cell at a time, both before and after it is lysed. This allows researchers to identify cells of interest (for example certain populations of immune system cells), lyse the individual cells, and to then analyze the resulting debris. When transmitted down a flow chamber, these cells can be identified and analyzed in an efficient and meaningful manner.

The analysis can include combining at least one of the cell's surface marker and the cell's morphological data (cell surface indicia) with the data from the at least one molecule present in one of the cytoplasm and the nucleus of the cells (cell interior indicia) to produce a population analysis of the cells. This population analysis can then be used to reach sound scientific conclusions about the cell population. The cell surface indicia can be analyzed while the cells transit the microfluidic pathways. The cell debris can also be analyzed for one or more cell interior indicia molecules while the cells transit the microfluidic pathways. The cells can be alive at the start of the process, or alternatively dead and optionally treated by one or more chemical fixative solutions.

In the embodiments described herein, the invention provides a combination device and method that draws upon a diverse array of known techniques. The various techniques and device sub-components that are suitable for the different functions of the present invention are described below.

In one embodiment, a method for performing a population analysis on a plurality of cells while in transit in at least one dynamic microfluidic pathway. The process includes first providing a population of cells having cell surface indicia, then transmitting the population of cells through the microfluidic pathway. Once in the pathway, the method includes analyzing the cell surface indicia, then subsequently lysing at least one cell while it transits a microfluidic pathway to produce cell debris exposing cell interior indicia. The cell interior indicia found in the debris is then analyzed for at least one molecule or cellular component that may be present in said cell interior indicia.

The method may further include a step or steps in which said cell surface indicia are selected from the group consisting of cell size, cell shape, cell morphology, cell narrow angle light scattering, cell wide angle light scattering, cell electrical characteristics, cell surface membrane molecules, and cell surface markers. The cell interior indicia may be selected from the group consisting of cell cytoplasmic-side membrane molecules, cell cytoplasm molecules, cell nuclear membrane molecules, cell nuclear molecules, DNA, RNA, cell interior proteins, cell interior lipids, cell interior carbohydrates, cell interior cofactors, cell interior ions, cell interior ATP, cell organelles, and cell organelle molecules.

The method may further include combining data from at least one of the cell's surface indicia and data from at least one of the cell's interior indicia from a plurality of said cells to produce a population analysis of said cells. At least one of the cell surface or cell interior indicia may be analyzed while the cells transit the microfluidic pathway, and the cells may be alive as they enter the microfluidic pathway.

In another embodiment, generally, a method is provided for performing a population analysis on a plurality of cells, in which the plurality of cells is analyzed on an individual cell-by-cell basis for specific cell surface markers or specific morphological characteristics, and the individual data obtained on a cell-by-cell basis then assembled into a statistical analysis of the population of cells. The method may include first providing a population of cells, then causing the population of cells to travel through a microfluidic pathway, and analyzing the population of cells as they do so. Then the method includes lysing the cells, then analyzing the lysed cells. The method of lysing the cells (cell lysing method) may be a method selected from the group consisting of electrical lysing, chemical lysing, osmotic lysing, ultrasonic lysing, laser lysing, and heat lysing methods.

In yet another embodiment, the methods for analyzing the specific cell surface markers or specific morphological characteristics may be selected from the group consisting of electrode based electronic measuring methods, light scattering methods, fluorescence detection methods, luminescence detection methods, light absorbance detection methods, and automated video microscopy vision recognition methods.

The step of causing the cells to travel through a microfluidic pathway may use a moving fluid stream either with or without a sheath fluid, and may be capable of transporting the individual cells through at least part of the microfluidic pathway in an intact state. The method of lysing the cells may lyse the individual cells while the cells are transiting through the microfluidic pathways.

The method of analyzing the lysed cells may be a biochemical analysis method selected from the group consisting of fluorescent ion indicator methods, luminescent ion indicator methods, chromogenic enzyme substrate methods, fluorescent enzyme substrate methods, luminescent enzyme substrate methods, fluorescent antibody methods, enzyme labeled antibody methods, luminescent antibody methods, molecular beacon methods, genetic analysis device methods, fluorescent nucleic acids methods, and luminescent nucleic acid methods.

The method of analyzing the lysed cells may further compensate for the distorting effects caused by the variable volume of the cell lysis field by incorporating a fluorescent or luminescent tracking dye into the cells before lysis, and also monitoring the fluorescence or luminescence distribution of the tracking dye when it is released from the cells after the cells are lysed.

A processor may be used to analyze the cell surface markers or the cell morphological characteristics and to lyse the cells based upon a comparison between the cell surface makers or cell morphological characteristics and previously determined cell surface marker or morphological characteristic data.

The method of population analysis may use a processor to analyze the cell surface markers or the cell morphological characteristics. The analysis may include first obtaining a first set of data pertaining to the cell surface markers or the cell morphological characteristics of the individual cells, then using the processor to biochemically analyze the cytoplasm or nuclear debris field of the lysed cells. A second set of data may then be obtained that pertains to the one or more molecules present in the cell cytoplasm or the nucleus of the individual cells. The process then includes using the processor is configured to correlate the first set of data and the second set of data according to user determined criteria, where the results of this correlation are either stored or transmitted.

In an embodiment of a device configure according to the invention, a device for correlating an individual cell's cell surface markers or cell morphological characteristics with one or more molecules present in the cell cytoplasm or nucleus of the individual cells is provided, where the device is capable of operating on a plurality of individual cells selected from a population of cells. The device may include one or more microfluidic pathways containing a moving fluid stream capable of transporting the individual cells through at least a portion of the microfludic pathways in an intact state. It may further include at least one transit analyzer configured to analyze the cell surface markers or the cell morphological characteristics of the individual cells while the cells are transiting the microfluidic pathways in an intact state. A cell lyser is configured to lyse the individual cells while the cells are transiting the microfluidic pathways to expose a cytoplasmic and nuclear debris field. At least one biochemistry analyzer is configured to biochemically analyze the cytoplasmic or nuclear debris field of the lysed cells for the one or more molecules present in the cell cytoplasm or the nucleus of the individual cell.

The cell lyser may be selected from the group consisting of electrical lysers, chemical lysers, osmotic lysers, ultrasonic lysers, laser lysers, and heat lysers.

The transit analyzer may be used to analyze the cell surface markers or the cell morphological characteristics is selected from the group consisting of electrode based electronic sensors, light scattering sensors, color detection sensors, fluorescence detection sensors, luminescence detection sensors, and automated video microscopy vision recognition sensors.

The microfluidic pathways of the device may carry the cells in a moving fluid stream that is protected from contact with at least one wall of the microfluidic pathways by a sheath fluid.

The biochemistry analyzer may be configured to analyze the debris field of the lysed cells utilizes biochemical reagents selected from the group consisting of fluorescent ion indicators, luminescent ion indicators, chromogenic enzyme substrates, fluorescent enzyme substrates, luminescent enzyme substrates, fluorescent antibodies, enzyme labeled antibodies, luminescent antibodies, molecular beacons, genetic analysis devices, fluorescent nucleic acids, and luminescent nucleic acids.

The biochemistry analyzer may corrects for the distorting effects caused by the variable volume of the cell lysis field by also monitoring the fluorescence or luminescence distribution of a cell cytoplasm tracking dye that is released upon cell lysis.

A processor may be connected to the transit analyzer and the cell lyser, in which the processor uses data obtained from the transit analyzer to control the operation of the cell lyser.

A processor may be connected to the transit analyzer, and it may obtain a first set of data pertaining to the cell surface markers or the cell morphological characteristics of the individual cells. The processor may also be connected to the biochemistry analyzer to biochemically analyze the cytoplasm or nuclear debris field of the lysed cells. The processor may then obtain a second set of data pertaining to the one or more molecules present in the cell cytoplasm or the nucleus of the individual cells, and may also correlates the first set of data and the second set of data according to user determined criteria and store or transmit the correlated data.

In yet another embodiment, a device is provided for correlating an individual cell's cell surface markers or cell morphological characteristics with one or more molecules present in the cell cytoplasm or nucleus of the individual cells, where the device is capable of operating on a plurality of individual cells selected from a population of cells. The device may include one or more microfluidic containing a moving fluid stream capable of transporting the individual cells through at least a portion of the microfludic pathways in an intact state. It may further include a transit analyzer to analyze the cell surface markers or the cell morphological characteristics of the individual cells while the cells are transiting the microfluidic pathways in an intact state, and also a cell lyser to lyse the individual cells while the cells are transiting the microfluidic pathways. The device may include a biochemistry analyzer to biochemically analyze the cytoplasmic or nuclear debris field of the lysed cells for the one or more molecules present in the cell cytoplasm or the nucleus of the individual cell, and a processor configured to process data collected from the transit analyzer to analyze the cell surface markers or the cell morphological characteristics to operate either the cell lyser or the cell biochemistry analyzer.

The processor may be configured to obtain a first set of data pertaining to the cell surface markers or the cell morphological characteristics of the individual cells, and the processor may be configured to obtain a second set of data pertaining to the one or more molecules present in the cell cytoplasm or the nucleus of the individual cells. The processor may also be configured to correlate the first set of data and the second set of data according to user determined criteria and store or transmit the correlated data.

The processor may also be configured to obtain a first set of data pertaining to the cell surface markers or the cell morphological characteristics of the individual cells, compare the first set of data with one or more preset user criteria, and vary the operation of the cell lyser to lyse the individual cells, where cells that meet one or more preset user criteria are lysed, and wherein cells that fail to meet one or more preset user criteria are not lysed.

The processor may also be configured to obtain a first set of data pertaining to the cell surface markers or the cell morphological characteristics of the individual cells, or wherein the processor is configured to obtain a second set of data pertaining to the one or more molecules present in the cell cytoplasm or nucleus of the individual cells; and wherein processor is configured to compare said first data or said second data with one or more preset user criteria, and alter the flow speed or flow direction of said cells or said cell debris through said microfluidic pathways when said first set of data or said second set of data meet one or more of said preset user criteria.

Nomenclature: Throughout this disclosure, the terms "fluid" and "buffer" will be used in an interchangeable manner. This is because the present application contemplates use with living cells and cell constituents, which are typically analyzed in an aqueous, pH controlled (buffered) fluid.

Throughout this discussion, those aspects of a cell's structure that can be determined by examining the cell's morphology or cell surface markers will occasionally be termed cell surface indicia. Cell surface indicia can include a cell's size, shape, internal structure as seen by light scattering or video microscopy, and can also include the biochemical status of the various molecules present on the exterior side of the cell's outer membrane. By contrast, those aspects of a cell's structure that can best be determined by biochemically analyzing one or more of the various molecules that are present on the inside of the cell, such as molecules present on the inner side of the cell membrane, the cell cytoplasm, or in the cell's various organelles such as the nucleus, mitochondria, lysosomes, etc. will occasionally be termed cell interior indicia.

The invention may utilize electrodes to measure cell size in flowing liquids, where some methods currently exist. The general principle is that when a cell, which is normally non-conductive, moves between two closely spaced electrodes in an aqueous fluid that contains ions (e.g. a saline buffer), the cell acts to momentarily impede the direct passage of ions between the two electrodes. Just as traffic must travel a longer distance when being diverted by an obstacle, the ions in the fluid must momentarily travel around the space occupied by the cell. As a result ion arrival at the opposite electrode is delayed by a small fraction of a second. When a rapidly oscillating (AC) electrical current is passed between the electrodes, this delay manifests itself (can be detected) as a momentary phase change. This effect also shows up as an electrical resistance change.

It has been observed that larger cells and particles cause more obstruction, resulting in a larger phase change or resistance change, and this effect can be utilized to allow the size of the cell to be deduced. Such electrode methods may be adopted for use in microscale flow cytometers, these methods may be employed into the combination cell surface and cytoplasm analytical device and methods configured according to the invention. For these purposes, the methods of Gawad et. al, "Micromachined impedance spectroscopy flow cytometer for cell analysis and particle sizing", Lab on a Chip, 2001, 1, 76-82; or alternative methods, may be used. These and other methods are known to those skilled in the art, who also will understand that the use of such techniques would not depart from the spirit and scope of the invention, which is defined by the appended claims and their equivalents.

In Gawad's method, the cells are passed through a relatively small opening in a microcapillary flow channel. This opening is typically often only a few tens of microns wide (e.g. Gawad teaches 20 micron openings). The electrodes, which will also have dimensions on the order of tens of microns, can either be placed side by side (separated by a gap) on a single surface of the channel, or alternatively can be placed on opposite sides of the channel. The electrodes can be produced by a variety of different micromachining or conductive material depositing techniques. The channel itself will often be formed from glass or other material. This material will ideally be transparent so as to facilitate some of the other optical techniques contemplated herein. A high frequency electrical current, typically in the 1-3 MHz range, is passed between the electrodes. This can then be analyzed by the methods of Gawad, and transformed by algorithms (such as those used by Gawad) into cell volume and diameter estimates.

Alternatively, the electrical resistance measurement methods taught by Koch. et. al, Journal of Micromechanics and Microengineering, 1999, also may be used.

In addition to being used for purposed of correlation with the cytoplasm or nuclear biochemistry, the cell volume signal may also be used to help synchronize other processes, contemplated by the present disclosure, such as release of appropriate reagents, timing of optical measurements, timing of cell lysis mechanisms, etc. As previously discussed, an apparatus configured according to the invention will typically have processor or other computing means, such as a microprocessor or logic or computational circuitry, that is capable of making appropriate decisions based upon the type of cell found to traverse the electrode. As described herein, a processor utilized in a system may be a dedicated microprocessor implemented on an integrated circuit, a general-purpose computer, or may be simple logic circuitry configured to perform necessary operations for computations needed for normal operation of the device, and may include other operations related to general or specific operations of the device. In this context, those skilled in the art will understand that describing a device or system that utilizes a processor to perform a function or task is not limited to any particular type of computational device, system or other means. Thus, a processor may be instructed to perform the proper steps it detects that a particle of the appropriate size has passed, but otherwise ignore particles of improper size, thus saving on reagent expenses and allowing the cell lysis and optical measurement means more time to regenerate between cells.

As a practical example, if only one cell in 100 has an appropriate size or internal structure (as determined by electrode or light scattering techniques), to be of potential interest to the investigator, then the processor can be programmed to ignore (not attempt to lyse) the 99 cells that don't meet the criteria. This single step reduces the amount of cytoplasmic debris (sticky nucleic acid strands, sticky cell debris) by a factor of almost 100, and helps prolong the period of time that the device can operate without clogging. Thus by combining appropriate cell pre-screening means with appropriate computational means capable of malting fast, real-time, decisions as to which cells to lyse or study further, robust and practical devices can be implemented.

In research, with FACS devices (discussed above), it has been observed that much useful information about the morphology of a population of suspended living cells can be deduced by light scattering techniques. This is usually done before the actual fluorescence analysis phase, and this light scattering data is proven to be extremely valuable. Light scattering data allows the computing means attached to the FACS machine to determine which cells in the cell population are worthy of further study, and which cells represent debris or unwanted background data. These methods are also contemplated for use in devices and methods configured according to the invention.

In general, when cells are moved through a narrow stream of fluid, and exposed to a beam of focused light (such as a laser beam), the amount of forward scattered light (that is light only slightly deflected from the original angle of the beam), is proportional to the size of the cell. By contrast, light scattered at greater angles provides information about the internal morphology of a cell. A cell with many small cytoplasmic granules will tend to have more side-scattered light. Thus, using forward and side scattered light, cell populations can be divided into small, medium, or large size, and into simple moderate or complex internal structures. This allows the FACS machines and other cell analyzers to be programmed to examine particular cell types of interest (e.g. distinguish between lymphocytes, monocytes, and neutrophils), and ignore cells and cell debris that is not of relevance to the particular experiment at hand.

In one embodiment, a device or system configured according to the invention can normally contain cell light scattering detection systems or devices capable of monitoring forward and side scattered light, as well as computing (or computational) systems or devices to analyze this data. Typically these computational systems or devices may be one or more processors, such as microprocessors for example, memory devices, input output devices, device subcomponent interface systems, actuator systems, and other systems or devices. In one embodiment, a device or system configured according to the invention may use data to operate the device according to investigator preference, and determine which cells to attempt to lyse, which cells to attempt to analyze further, and which cells to ignore.

Methods to lyse cells by brief pulses of electrical current are known in the art, and prior art methods, or alternative methods, may be used in the device disclosed here. Which particular method step or steps to incorporate would depend on the particular application at hand, as well as its parameters and goals. The invention contemplates use of various existing methods and steps and also future methods and steps that optimize devices and methods configured according to the invention. Such methods include Han et. al. "Fast Electrical Lysis of Cells for Capillary Electrophoresis", Anal. Chem. 2003, 75, 3688-3696; U.S. Pat. No. 4,832,814 to Root; U.S. Pat. No. 6,783,647 to Culbertson; U.S. Pat. No. 7,176,018 to Tai et. al.; US patent application 20040058423 to Albritton; US patent application 20060134777 to Lee; and others.

U.S. Pat. No. 7,176,018 to Tai teaches a micromachined cell lysis device with electrodes that are spaced by less than 10 μm from one another. In this disclosure, the cells are attracted to the space between the electrodes and then lysed. One drawback of this approach, however, is that in order to use the low-voltage methods contemplated by Tai, the dimensions of the device must be extremely small. This reduces cell throughput, and increases the chance that cells and cell debris will rapidly foul the device.

Krylov et. al., "Instrumentation for Chemical Cytometry", Anal. Chem. 2000, 72, 872-877, discloses and teaches a capillary electrophoresis method in which single cells are injected into capillary tubes, lysed by ultrasonic sound, strong electric fields, low ionic strength buffers or surfactants, and the contents of the tube then analyzed. Although Krylov did not chose to extend this type of method to systems capable of analyzing more than one cell at a time, or to continuous flow devices, the cell lytic methods taught by Krylov tend to be more suitable to high-throughput devices, such as the high throughput devices contemplated by the invention, because the larger voltages enable larger separation between the walls of the device, thus reducing the chance of device fouling as a result of cells and debris.

Other microdevice cell lysis methods may also be used in devices and methods configured according to the invention. These methods include, but are not limited to, optical (laser) lysis, focused ultrasound, chemical lysis (e.g. by use of surfactants such as sodium dodecyl sulfate (SDS), or appropriate molecules such as complement), microwave or heat-pulse lysis, etc.

McClain, "Single cell lysis on microfluidic devices", Proceedings of the uTAS 2001 Symposium—ornl.gov, teaches an alternative cell lysis method that may be employed. As McClain teaches, it is often advantageous to incorporate low (less than lytic) levels of a chemical (such as the surfactant sodium dodecyl sulfate [SDS]) into the cell's suspension fluid. Although the low levels of surfactant are not in themselves enough to lyse the cells, the surfactant weakens the cell membranes enough as to render the cell more susceptible to a later electrical lysis step. These methods and various different cell lysis methods are contemplated by the invention. Low (pre-lytic levels) of surfactant will tend to render a cell more susceptible to any lytic method, because the cell membrane is more fragile. Thus, cells suspended in pre- or sub-lytic levels of surfactant can be lysed by a greater variety of means, because a gentler (lesser) lytic stimulus is now needed. This allows the cells to be run in larger capillary channels, thus enabling use of alternative methods (such as the sheath flow methods discussed next), and reducing the chances that cells and cell debris will foul the device. Additionally, the surfactant present in the cell transport fluid will tend to help solublize or dissolve the post-lysis cytoplasmic debris, promoting biochemical analysis of the cytoplasm and nucleus, and also helping to further reduce the chance that cell debris will foul or clog the device.

In one embodiment of the invention, sub-lytic levels of surfactant (such as SDS, NP-40, Triton X-100, Tween, or other surfactant) will be present in the cell transport buffer or fluid. This cell transport buffer/fluid will also preferably contain buffering means to achieve the desired pH range (generally between pH. 6.0 to 8.0), and enough salt to maintain a roughly physiological osmotic concentration. Note that in some cases, however, it may be desired to deviate somewhat from normal osmotic concentrations in order to render the cells still more susceptible to lysis when the cells reach the lytic region of the apparatus.

In one embodiment of the invention, sheath flow techniques can be used to better transmit cells through the microfluidic pathways of a device configured according to the invention. Sheath flow techniques are often used to move cells through small-channel devices, such as capillary tubes, fluorescent cell sorters, and microfabricated devices. Sheath flows encase the fluid containing the cells (cell carrier fluid) in a second, outer-wrapper, of cell-free fluid. As a result, the chance that the cells or cell-debris will come into contact with the walls of the device are reduced. This reduces the chance that the debris will foul the device, and prolongs the useful lifetime of the device. Although sheath fluid methods will generally be unnecessary when the cells do not show a great tendency to stick to the walls of the device, or when cell lysis does not generate an overly "sticky" cytoplasmic or nuclear residue that sticks to the walls of the device, sheath fluid methods can be useful when "sticky" cells or cells with "sticky" cytoplasmic residue are used.

Some recent work on such sheath-flow devices includes Wolf et. al., "Integrating advanced functionality in a microfabricated high-throughput fluorescent-activated cell sorter", Lab Chip, 2003, 3, 22-27; and Niewenhuis et. al., "Integrated flow-cells for novel adjustable sheath flows", Lab Chip, 2003, 3, 56-61; and Munson et. al, "Suppression of non-specific adsorption using sheath flow" Lab Chip 2004, 4, 438-445. These methods are generally suitable for the devices, systems and methods contemplated to be configured according to the invention.

Methods to detect the presence or absence of specific molecules (antigens) on cell surfaces are well understood in the art, and thus may be incorporated by devices and methods configured according to the invention. One common method is to produce antibodies (often monoclonal antibodies) or antibody fragments (such as Fab fragments) against the cell surface antigen (component) of interest, and label these antibodies with one of a very broad array of fluorescent or luminescent moieties or particles (e.g. fluorescent dyes, fluorescent microspheres, quantum dots, green fluorescent protein hybrids, etc.). These methods have been reviewed in many publications (e.g. Zhang et. al. "Creating new fluorescent probes for cell biology", Nature Reviews, Molecular and Cell Biology, Vol. 3, page 906-918, December 2002) The Molecular Probes division of Invitrogen Corporation presently provides many commercially available reagents useful for these methods, and other corporations do so as well.

A number of alternative cell cytoplasm or nucleic acid labeling methods are known in the art. These are reviewed by Zhang, (Zhang et. al. "Creating new fluorescent probes for cell biology", Nature Reviews, Molecular and Cell Biology, Vol. 3, page 906-918, December 2002). This reference also discusses many cell cytoplasm-labeling methods as well. As previously discussed, the Molecular Probes division of Invitrogen Corporation, also provides cell cytoplasm reagents on a commercial basis.

Some further examples of cell cytoplasm or nucleic acid labeling methods include ATP labeling, Ion labeling, Enzymatic labeling, Nucleic Acid Labeling, and "Gene Chip" methods, which are discussed in more detail below. Such methods and other methods are contemplated by the invention, and are in no way limiting to the invention, which is defined by the appended claims and their equivalents.

To determine cellular ATP levels, it often is advantageous to use bioluminescence ATP assays. Typically such assays work by the luciferase mediated chemical reaction:

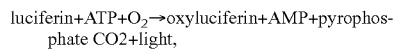

luciferin+ATP+$O_2$→oxyluciferin+AMP+pyrophosphate CO2+light, where the light (typically measured at around 560 nm using a luminometer), is proportional to the amount of ATP in the sample. Here the flow chamber methods of Boudreault and Grygorczyk, "Cell swelling-induced ATP release is highly dependent on intracellular calcium elevations", J. Physiol. 561.2 (2004) pp 499-513 can be used.

Alternatively, smaller format methods, such as the methods of Young et. al., "Monitoring enzymatic reactions in nanolitre wells", Journal of Microscopy, Vol. 212, Pt 3 Dec. 2003, pp. 254-263, may also be used.

Cell ions can be assayed by incorporating fluorescent ion selective probes into the cell transport buffer shortly before, during, or immediately after lysis. Various methods suitable for the present disclosure are disclosed in Johnson, "Fluorescent probes for living cells", The Histochemical Journal 30(3), pages 123-140, March 1998).

Many cellular components of interest are enzymes, and here, fluorescent, luminescent or electrochemical enzyme substrate assay methods may frequently be appropriate. Although electrochemical enzymatic detection methods may be used (as in the methods of Cai et. at, "Ultra-Low-Volume, Real-Time Measurements of Lactate from the Single Heart Cell Using Microsystems Technology", Anal. Chem. 2002, 74, 908-914"), such methods will generally be less often used because of problems of electrode fouling. As a result, optical methods (fluorescence, luminescence, and rarely calorimetric measurements) are generally preferred.

When cell cytoplasm enzymes, such as caspase enzymes, are being investigated, it often will be advantageous to use chemically tagged substrates that are altered by the enzyme from a non-fluorescent or non-luminescent form to a fluorescent or luminescent form. Examples of such substrates include the Rhodamine 110 protease substrates of Mangel, et. al. (U.S. Pat. No. 4,557,862), and other substrates. Various other methods suitable for the present disclosure are disclosed in Johnson, "Fluorescent probes for living cells", The Histochemical Journal 30(3), pages 123-140, March 1998).

In certain cases, it may be advantageous to probe the state of the cell's cytoplasmic or nuclear RNA or DNA using nucleic acid probes. Although many types of nucleic acid probes may be used, the short dwell times and difficulty in doing PCR style thermal cycling in a flow-through microcapillary device must be reckoned with. Here, methods that work relatively quickly and in a homogenous format (not requiring separation steps) tend to be preferred. One example of a suitable nucleic probe method is the molecular beacons method, which is a technology currently known by those skilled in the art.

Molecular beacons allow nucleic acid assays to be done in a comparatively rapid and homogenous format. Molecular beacons are hairpin RNA probes that, in the absence of a target gene, will normally snap back on themselves. The two ends of the molecular beacon RNA probe contain complementary fluorescence emission and absorbance moieties, such that when the probe is in the snapped back configuration, fluorescence emitted by one moiety is absorbed by the other moiety, resulting in efficient fluorescence quenching. However when a target gene is present, the gene will hybridize to one of the RNA hairpin strands preventing the hairpin from snapping back and allowing the fluorescence moiety to fluoresce with high efficiency. Here, the methods described in U.S. Pat. No. 6,949,343 of Coull et. al, or other similar methods may be used.

A wide variety of alternative nucleic acid"chip" methods are suitable for devices, systems and methods configured according to the invention. These methods typically work by binding a series of nucleic acids of interest to a solid surface, and using marker means (often a fluorescent label) to detect when a cell nucleic acid material of interest binds to the "chip" nucleic acid. Those skilled in the art will understand that such methods are well known and not limiting to the invention.

Cell debris from cells lysed in continuous flow devices tends to expand in volume, due to diffusion and turbulence effects. Immediately after lysis, the volume of the cell debris is simply that of the original cell, but as time continues, the cell debris occupies an ever-expanding volume. For simple devices in which the cell cytoplasm is lysed in a small volume, no dilution correction may be necessary.

For larger devices however, such as sheath flow devices, it may be advantageous to determine the extent (volume) now occupied by the cell cytoplasm debris field in the moments after cell lysis, and use this debris field volume data to correct the assay data for distortions caused by variations in the volume of the cytoplasm debris field.

Generally, it will be desirable to design the dimensions of the microcapillary flow-through device to constrain the volume of the cell debris to the maximum amount possible, given other constraints such as flow rate and the desire to avoid cells and cell debris clogging the assay. Examples of some of these dimensions are shown in the first embodiment of the invention Figure illustrated in FIGS. 1-4, and described in the accompanying text.

When sheath flow techniques are used, the volume of the debris field may be actively contained or "focused" by using fluid flow from inlet jets on either side of the main sample flow to "compress" the sample flow dimensions, following the methods of Nieuwenhuis, Lab Chip, 2003, 3, 56-61. Alternatively, inlet flow from inlet jets on either side of the main sample flow may be used to selectively defocus and refocus the cell debris field in order to facilitate mixing the cell debris field analytes with the reaction chemistry contained in the surrounding fluid.

Although proper device geometry and active or passive debris field focusing methods will often be advantageous, these methods may need to be supplemented by cell debris measurement techniques. Here, cells may be loaded with an appropriate marker, such as calcein, a membrane permeable dye that becomes fluorescent once the cell internalizes it. The dispersion of the calcein dye (also known as fluoreon, available from the Molecular Probes division of Invitrogen) after cell lysis may be monitored by the methods of McClain et. al., "Proceedings of the uTAS 2001 Symposium"—ornl.gov, or other methods.

Outside the cell, calcein exists in a non-fluorescent form. However when transported into the cell, cellular enzymes convert the dye to a fluorescent form. Monitoring the dispersion of a fluorescent or luminescent cytoplasm dye allows the cell cytoplasm biochemistry data to be adjusted, compensated, or normalized by the volume of the cell debris field.

An additional advantage of cell cytoplasmic volume marker probes such as calcein, and equivalent probes, is that it also allows the device to throw out or mark data from dead cells. Dead cells lack the appropriate conversion enzyme, and thus do not convert calcein to a fluorescent form. Thus dyes of this type have the additional advantage of allowing the device to discard any results that may have been obtained from dead cells, thus improving the accuracy of the assay.

If calcein is being used, it will typically be useful to monitor the debris field by fluorescence excitation at around 495 nm, and at around 515 nm. If use with luminescent cell component assay reagents, such as the ATP detecting reagent luciferin, is contemplated, it may also be desirable to operate the fluorescence excitation source in a pulsed mode so that the luminescent signal can be observed during the periods when the fluorescence excitation pulse is off. In this way, the concentration of the cell component and the volume of the debris field can be determined in a nearly simultaneous manner, and distortions due to variable volume and dilution may be minimized.

As previously discussed, usually a carrier buffer will carry the cells and cell constituents. Often this buffer will contain physiological saline, appropriate ions to maintain cell viability and prevent the nucleic acids in the lysed cells from becoming totally denature, such as calcium and magnesium, small amounts of SDS or other surfactant to mildly weaken the cell membrane, and help solublilze the lysed cell components, and cell debris tracking dyes such as calcein.

A sheath fluid buffer will generally consist of physiological saline and a surfactant (used to help keep the sides of the glass clean), as well as other agents used to help prevent cell debris from clogging the apparatus such as magnesium and other ions. Carrier proteins such as albumin may also be used as situations warrant.

FIG. 1 is a diagrammatic view of a first embodiment flow lysometer configured according to the invention to correlate red cell size with red cell cytoplasmic ATP concentration. In this example configuration, a microcapillary channel of varying widths is etched (photoetched) or machined to into a solid substrate (101) such as PolyDiMethylSiloxane (PDMS) to a depth of about 3 microns, and are covered on the top by a transparent material such as glass, forming a narrow 3 micron high channel bounded on all four sides by a solid material (except at the entry and exit ports), through which buffer may flow. Cells (in this example, red cells) (102) enter the device at entry port (103) suspended in a 100 mM phosphate buffered saline, pH 7.4, 310 mosmol carrier buffer that also contains Luciferin and Luciferase. The cells and carrier buffer are propelled through the device by an electro-osmotic pumping effect produced by a bias voltage from electrical power source (104), which in this first embodiment was set to a 50-volt bias voltage.

As the red cells traverse the lysometer, they first encounter electrical cell counter and size monitoring electrodes (105) and (106). These electrodes, usually composed of a thin layer of gold, have a width of about 10 microns each, and are separated by a distance of about 10 microns each from each other. These are formed side by side on the floor of the capillary channel.

Electrodes (105) and (106) are electrically coupled to an external electrical circuit capable of monitoring changes in the electrical impedance or resistance between the electrodes (105) and (106). As the cell passes the electrodes, ions traveling between the two electrodes have to traverse a somewhat longer and also somewhat narrower path, and this causes a phase change and/or a resistance change between the two electrodes.

In the first embodiment experimental apparatus of FIG. 1, this change is proportional to the diameter of the channel (D), the channel length (L), the particle (red cell) diameter (d), and the electrical resistance of the buffer, (R) according to the formula derived by Koch. et. al, Journal of Micromechanics and Microengineering, 1999:

$$\frac{\Delta R}{R} = \frac{D}{L}\left[\frac{\sin^{-1}\frac{d}{D}}{\left(1-\left(\frac{d}{D}\right)^2\right)^{\frac{1}{2}}} - \frac{d}{D}\right]$$

Thus, by using capillary dimensions of known size, and by detecting a momentary voltage or impedance change between the two electrodes, the effective diameter (here the cell morphological characteristic of interest is diameter) of the red cells as they traverse the device may be determined. (As an example, channel length L can be 40 microns, the electrode width can be 5 microns, the channel width can be 10 microns, a 15-volt potential difference can be put between the two electrodes, and the signal can be measured with DC signal amplifier with a gain of 850.)

As the cells traverse the device, they become ruptured in a cell lytic zone (107). The ATP in the cell cytoplasm mixes with the luciferin and luciferase in the carrier buffer or fluid (102), producing light 108, which is detected by a microscope (109) equipped with an electronic light sensor. Excess reaction material (110) was then discarded.

Figure 2:
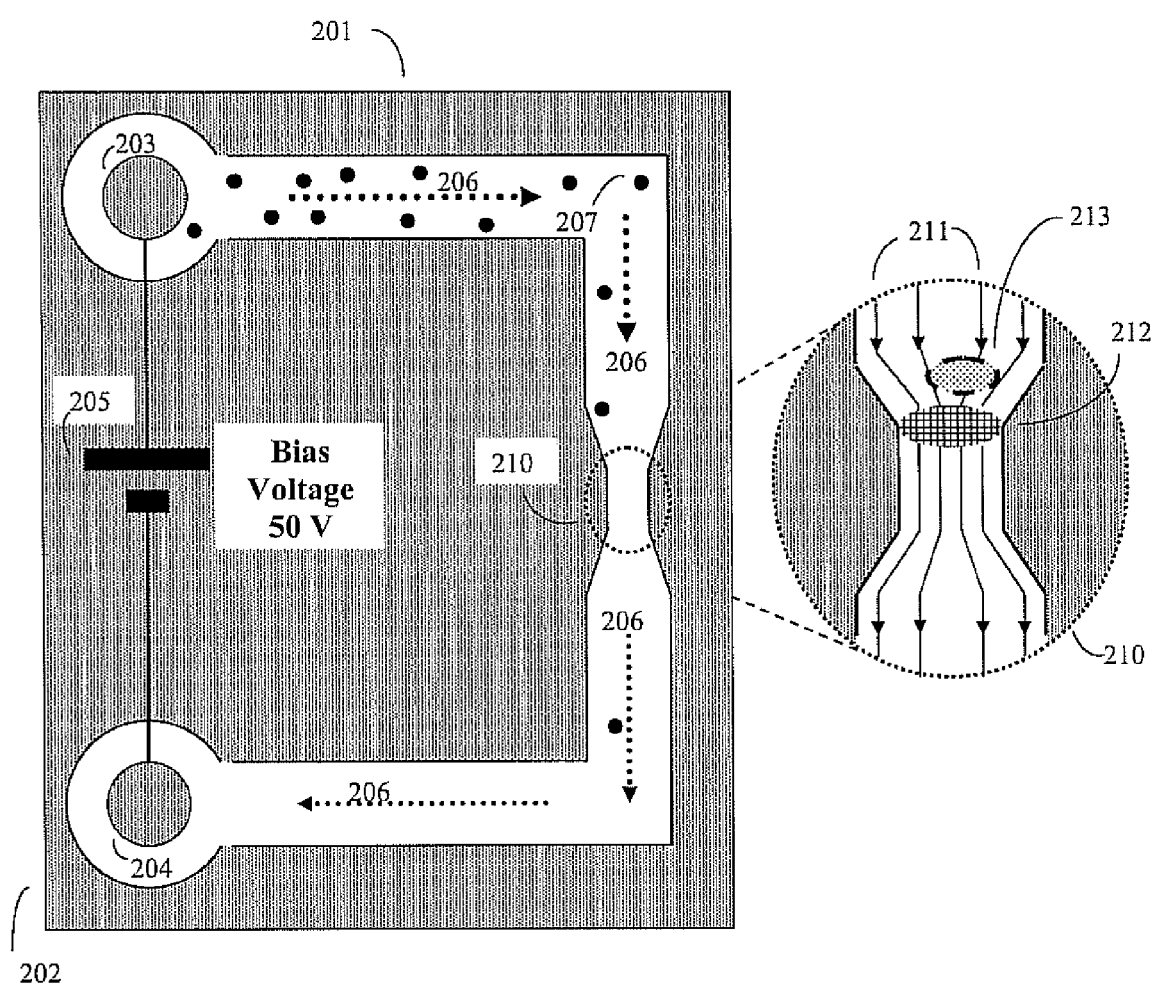
FIG. 2 shows a diagram of the electronic cell counter used in one embodiment of the invention.

FIG. 2 illustrates a top view of the first embodiment device of FIG. 1. The overall dimensions of this first embodiment are 0.6 cm (201) by 0.7 cm (202). Electrodes (203) and (204) connected to electrical potential source (205) provide the electroosmotic driving force to drive the cells from the electrode (203) region of the device to the electrode (204) region of the device. This electroosmotic flow is shown as arrows (206). The small particles next to the arrows (207) represent the ion gradient created by the potential difference between electrodes (203) and (204), which is the driving force for the electroosmotic flow.

The lysing region of the device is shown in (210) in both normal and magnified views. The narrowest part of the lysing channel is about 10 microns (um) across. By contrast, the entry and exit regions of the lysing channel are about 200 microns across. As a result, the electrical field lines (211) become narrowed and focused at the entry to the lysing region (212). As a result, cells (such as red cells) are subjected to much force as they enter this lytic region, and are lysed. The cytoplasmic contents of the red cells are spilled into the buffer (fluid), and are transported out of the lytic zone by electroosmotic flow.

Figure 3:
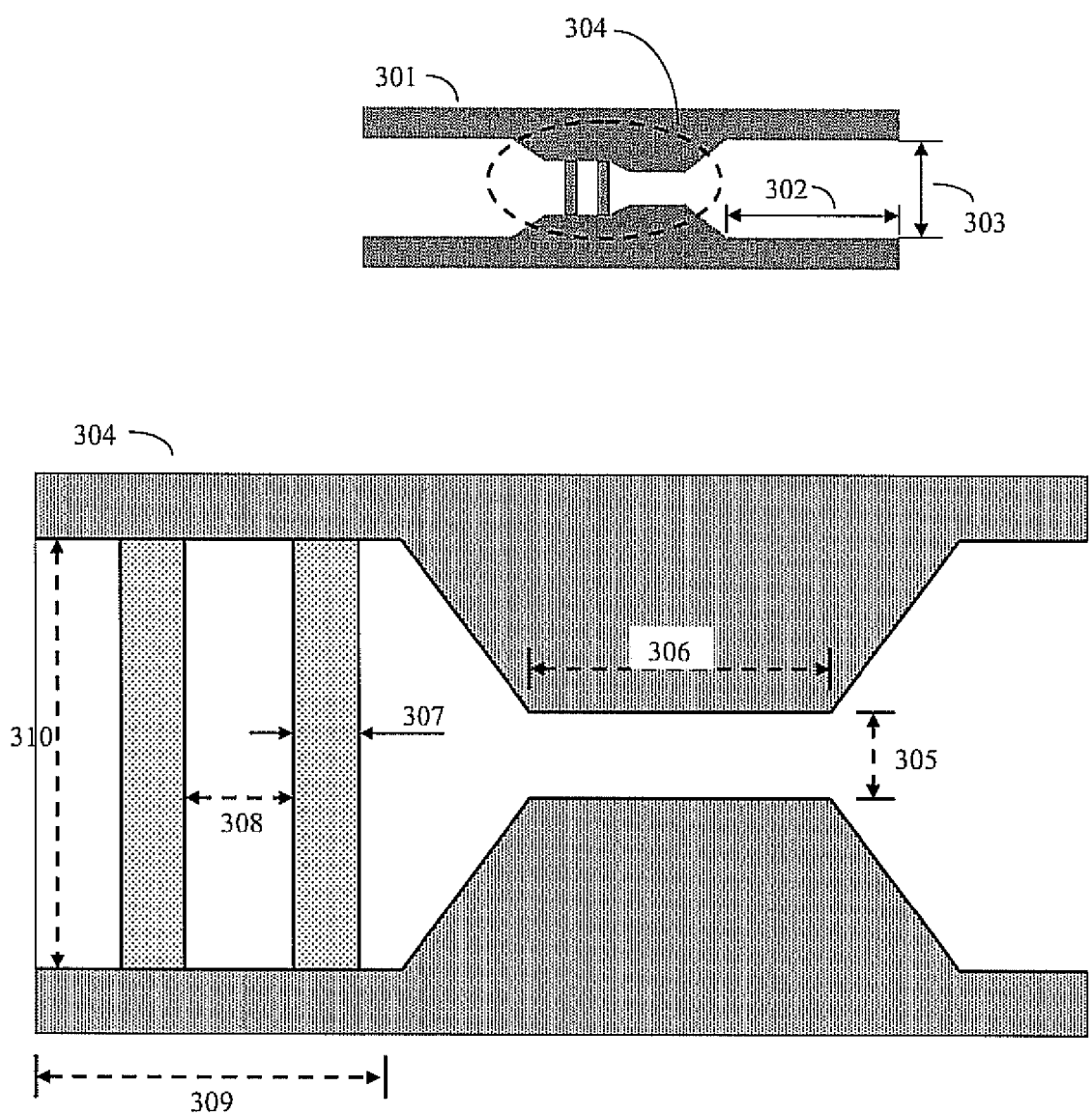
FIG. 3 shows a diagram of the electroosmotic pump used in one embodiment of the invention.

FIG. 3 shows some of the dimensions of the first embodiment flow lysometer device (301) previously shown in FIGS. 1 and 2. The dimensions of the post-lytic analytical chamber are approximately 2,000 microns (302) by (100 microns) (303). The lytic region of this device is shown as both a normal and magnified view in (304).

According to the invention, the dimensions of the cell lysis portion of the device (304) can vary. Some examples of these various dimensions are shown in table I below:

TABLE I

| Dimensions of the lytic portion of the flow lysometer | | | | | |
|---|---|---|---|---|---|
| Devices | | #1 | #2 | #3 | #4 |
| Sensing part | $W_S$ | 12 um | 16 um | 24 um | 32 um |
| Lysis part | $W_L$ | | 4 um | | 8 um |
| | $L_L$ | | 16 um | | 32 um |

Here $W_S$ corresponds to the length of 3(310), $W_L$ corresponds to the height of the lytic passageway denoted by 3(306) and 3(305), and $L_L$ corresponds to the length of 3(306). Note that $L_L$ is often four times the height of the passageway, so that if $W_L$ is 4 microns high, $L_L$ will be 16 microns long.

In these configurations, the width of electrodes 3(307) is 10 um, and the two electrodes are separated by a gap 3(308) of 10 microns. The width of region 3(309) is 50 microns. In the cell morphology-sensing region of the device, the height of this region was made somewhat smaller so that the cells were forced to squeeze against the electrodes as they pass into the lytic chamber. Thus in the first embodiment devices, the height of the region bounded by 3(309) and 3(310) is only 3 microns high.

In the first embodiment flow lysometer, the operating parameters of table 2 were used:

TABLE 2

| Operating parameters for the first embodiment flow lysometer | | | | | |
|---|---|---|---|---|---|
| Specifications | Variables | #1 | #2 | #3 | #4 |
| E-field in the lysis part | $E_L$ | | 1.2 kV/cm | | |
| Applied voltage | $V_n$ | 18.5 V | 18.0 V | 34.3 V | 33.8 V |
| Flow speed | $V_{flow}$ | ~80 um/sec | ~80 um/sec | ~160 um/sec | ~160 um/sec |
| Relative width of sensing channel | $W_s/D_{rbc}$ | 1.5 | 2 | 3 | 4 |
| Smallest channel width | $W_L$ | | 4 um | | 8 um |

Figure 4:
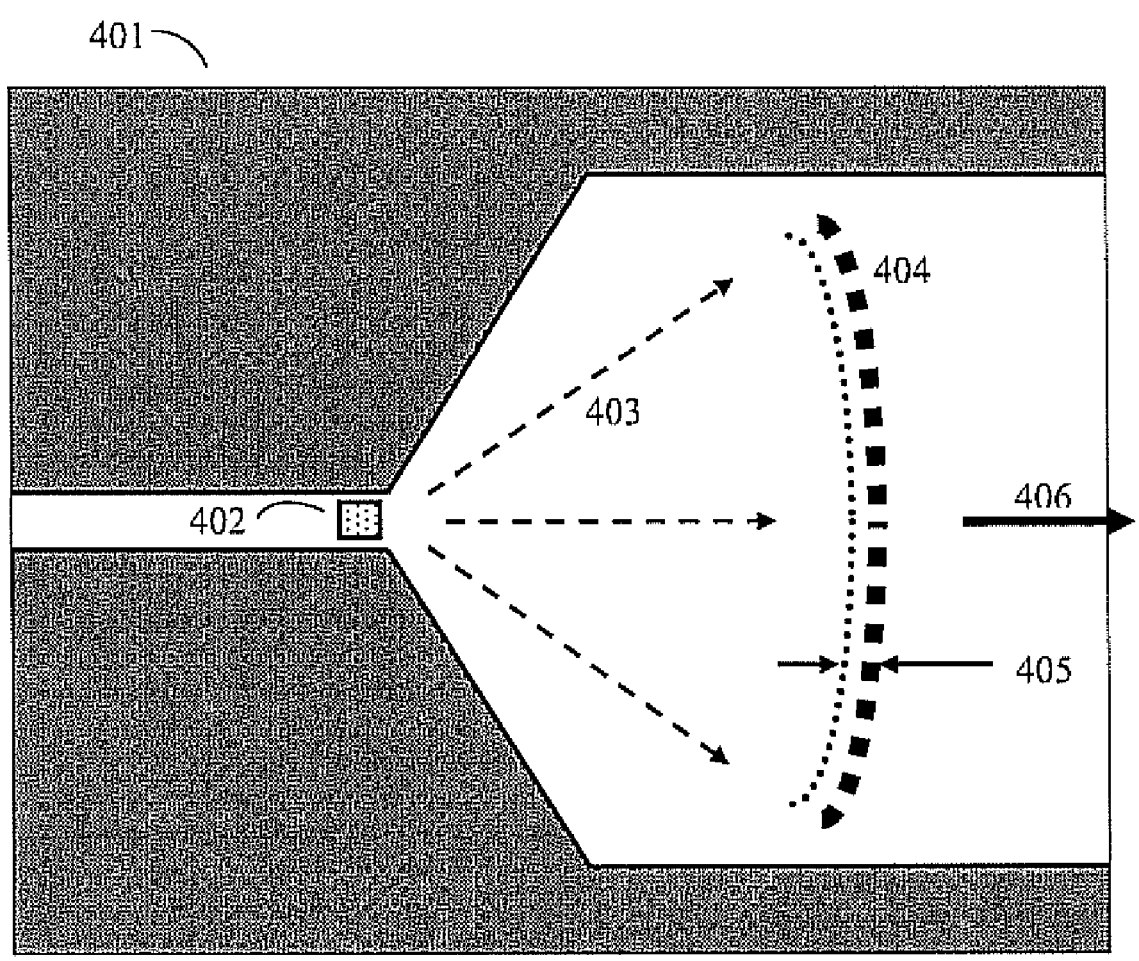
FIG. 4 shows an example of the biochemical signal produced by one embodiment of the invention.

FIG. 4 shows the how the first embodiment flow lysometer may detect cytoplasmic molecules. In this case, the cytoplasmic molecule is ATP. Other methods are contemplated, and, given this disclosure, those skilled in the art will be able to devise such methods without departing from the spirit and scope of the invention.

FIG. 4 shows the exit portion of the flow lysometer (401), showing the fate of the cell cytoplasm after the cell lysis step previously shown in FIG. 2. Immediately after lysis, the red cell cytoplasm (402) has an approximate volume of 8 microns by 8 microns by 4 microns. As the cytoplasm leaves the narrow (roughly 4-10 micron wide) lysis chamber channel, the cytoplasm encounters the much wider (100-200 micron wide) analytical region of the device. Propelled by the electroosmotic flow, the red cell cytoplasmic residue spreads out (403) into an arc or wave front of cytoplasmic residue (404). This arc (404) is relatively thin (405), with a width on the order about a micron. As this arc of cytoplasm spreads out, the ATP in the cytoplasm reacts with the luciferin and luciferase in the carrier fluid (or buffer), producing a moving luminescent arc that can be detected by a photodetector (not shown). The intensity of the luminescence is proportional to the amount of ATP present in the red cell. Eventually electroosmotic flow propels the cytoplasmic arc out of the chamber (406) and into either a waste receptacle, or alternatively into storage or another analytical device.

Figure 5:
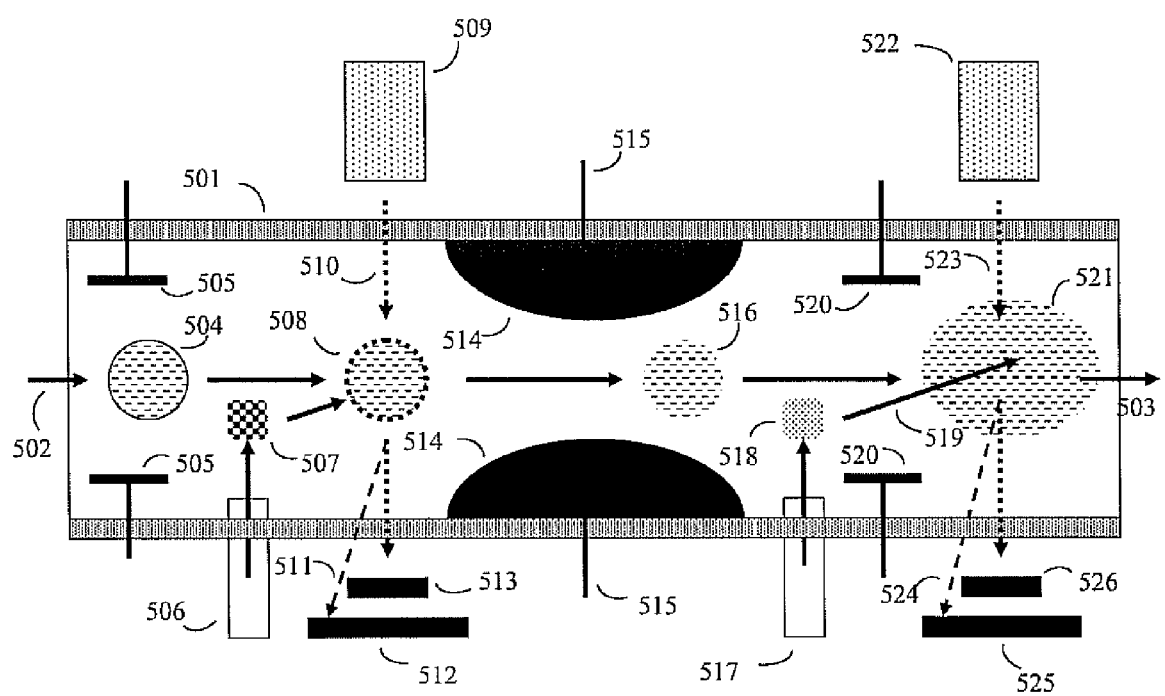
FIG. 5 shows a diagram of a higher functionality cell surface and cytoplasm analysis device.

FIG. 5 illustrates an alternative embodiment of the invention, another example, and is a diagram of a more complex flow lysometer device.

This embodiment may be constructed as one or more capillary channels etched or cut out of a larger substrate material, such as glass or plastic. This creates a hollow capillary channel bounded by walls (501) through which fluid (502), normally consisting of buffered isotonic saline is introduced at an entry side. This fluid normally exits at an exit side (503) and the fluid movement is often driven by either electroosmotic force or some other kind of pump, such as a mechanical pump (not shown). The fluid contains a suspension of living cells (504). As these cells enter the capillary channel, they pass through a narrow opening containing optional electrodes (505), which optionally monitor the cell's size by detecting electrical current resistance, or impedance changes, as described previously.

As the cell passes through the capillary channel, an optional reagent port (506) may inject reagents (507). Often these reagents may consist of cell surface marker analysis reagents, such as fluorescent antibodies directed against cell surface markers of interest. However these reagents may also include surfactants or other agents (such as complement) to weaken the cell membrane, and may also include a tracking dye to monitor the fluid containing a cell of particular interest as it passes through the channel, or some other dye, such as calcein, intended to monitor the cell cytoplasm fragmentation field after the cell becomes lysed in a later step. Reagents (507) may also include reagents intended to monitor the biochemical status of the cell's cytoplasm after the cell becomes lysed in a later step. In this example, the reagents (507) are a fluorescent antibody against a cell surface marker of interest, and these antibodies bind to the surface of cell (504) creating an antibody labeled cell (508).

Prior to lysis, the status of cell (508) may be monitored by additional optical techniques. These techniques may include optical (often laser) light scattering and/or fluorescence monitoring techniques and/or automated video microscopy vision analysis techniques. Typically an optical light source, such as a laser (509), will direct a focused beam of light (510) at cell (508). Depending upon the analytic method contemplated, cell (508) will scatter some of this light, (511), and the magnitude and direction of this scatter will give information relating to cell contents and morphology, and this may be detected by photodetector (512). Often photodetector (512) will be protected by baffle (513) from direct exposure to un-scattered light from the light source. If a fluorescence measurement is contemplated, then photodetector (512) will normally employ wavelength-filtering means (not shown) such as a bandpass filter to ensure that the only light that is observed is wavelength shifted fluorescent light. If fluorescence observations are contemplated, often light source (509) will further control the wavelength range of emitted beam (510) by an emission bandpass filter (not shown). Alternatively, the morphology of cell (508) may be monitored by video microscopy and an automated vision interpretation system, in which case detector (512) may be a microscope video detector. Depending upon the detection means chosen, the actual angle between the detector (512) and the illumination source (9) may vary. Although for simplicity, the drawing shows detector (512) located at an 180° angle from light source (509), in practice it will often be convenient to use a different angle, such as 90°, which will minimize interference from the direct beam (510).

After the optional pre-lytic optical analysis phase, the cell then moves into the lytic zone of the device (514). Here the cell may be lysed by one or more different means. The cell may pass into a lysing electrode (514) where the cell will be lysed by exposure to a high potential gradient. In this case, lysing zone (514) may be connected to an external electrical source via optional electrodes (515). Alternatively the lysing zone may expose the cells to a transient burst of ultrasonic energy, heat, light (e.g. a directed laser beam), or lytic chemical such as a surfactant such as SDS, in which case lysing zone (514) may be another reagent port.

In a preferred embodiment, the device will contain computing devices and systems that determine the cell size and other characteristics based upon data obtained from electrodes (5) and/or light scattering or fluorescence detectors (509), (510), (511), (512), (513). The computing devices and systems will determine if the cell characteristics meet predetermined criteria set by the experimenter on a rapid, real-time basis, and operate the apparatus accordingly. As an example, if the cell size as determined by electrodes (505) falls inside of the pre-selected size range, then the computing devices and systems may communicate with and cause the cell lyser in lysing zone (514) to lyse the cell, and/or add appropriate reagents through ports (506) and (517). However if the cell size falls outside of the pre-selected range, the computing devices and systems will communicate with and cause the cell lyser (514) not to attempt to lyse the cell, and also may not add reagents through ports (506) and (517). Such computing devices and systems (not shown) can thus both save on reagent costs and also reduce the probability that the device will become clogged by cell debris (516), (521).

After the cells are lysed in the lysing zone (514), the outer membrane of the cell will normally be in a non-intact state, exposing the contents of the cell's cytoplasm (516) to carrier buffer (502). As is shown, immediately after lysis, the cell's cytoplasm (debris field) will normally occupy a smaller area, which will tend to grow with time as diffusion and turbulence causes the cytoplasm to mix with the carrier buffer (502).

As the cell debris field continues to move along the capillary channel, it may pass a second reagent port (517) where one or more additional cytoplasm monitoring reagents may be added. These may be the ATP monitoring reagents luciferin and luciferase, or other reagents such as fluorescent or luminescent enzyme substrates, monoclonal antibodies, ionophores, molecular beacons, etc. as described previously. Typically these reagents will be introduced immediately after lysis, and if necessary the length of the capillary channel may be extended (not shown in the drawing) to allow time for the reagents (518) to fully penetrate into the debris field (516) and react (519) with the contents of the cell cytoplasm.

After lysis, the cell debris may pass through an optional set of impedance or resistance monitoring electrodes (520). These will typically be used to confirm the extent of cell lysis, and will provide an important source of control (verification) information to the system. As an example, an incompletely lysed or non-lysed cell (516) would not provide enough cytoplasmic contents to react properly with reagents (518). Without the second set of impedance or resistance monitoring electrodes (520), this would result in the device reporting an inaccurately low level of activity for the particular cytoplasm components being investigated. However with impedance or resistance monitoring electrodes (20), the system will know that the cell was not adequately lysed, and that this particular cytoplasm analysis should be discarded.

Note that for simplicity of explanation and understanding, electrode dimensional constraints (e.g. device wall configurations that force the cells up against the electrodes, as shown in FIGS. 1-4), are not shown in FIGS. 6-10, but may be assumed to exist where needed and appropriate.

After the cell cytoplasm debris (521) has had time to adequately react with reagents (518), the debris field then passes through a cytoplasm analysis zone. If fluorescent reagents are contemplated, this zone may include an optical light source, such as a laser (522) and optional bandpass filter (not shown). If luminescent reagents are contemplated, then light source (522) is either not needed, or alternatively (and usually preferably) operated in a pulsed mode in which luminescence determinations are made during the period in which light source (522) is off. Generally operating light source (522) in a pulsed mode is preferred because this enables light source (522) to be used to allow the system to monitor the relative distribution of cytoplasm volume markers, such as calcein, in the debris field, and correct the cytoplasm reagent results for the distorting effects of variable debris field volume.

Here the beam of light (523) from light source (524) enters the debris field (521) where it may interact with cytoplasm volume markers such as calcein, or alternatively interact with fluorescent enzyme substrates, antibodies, ionophore reagents etc. previously introduced through ports (506) and (517). Fluorescent (or luminescent) light emitted by the reagents (524) exits the debris field and is detected by photodetector (525). If fluorescence measurements are contemplated, photodetector (525) will usually have light filtering devices (not shown), such as a bandpass filter, diffraction grating, prism or other means to subtract the wavelengths of illumination beam (523) from the measurement.

Light scattering measurements may also be performed by light source (522), photodetector (525) and baffle (526) to monitor the status of the debris field. Alternately the status of the debris field may be monitored by video microscopy and automated image analysis techniques, in which case photodetector (525) will be a microscope video photodetector.

In yet another embodiment, multiple light sources (522) may be arranged so as to selectively heat portions of the cytoplasmic debris field (521) as it passes along the capillary path. This selective heating might be used to facilitate binding of nucleic acid probes to cell debris DNA or RNA.

If desired, after this stage of the analysis, the exit fluid flow (503) containing cytoplasm debris may be diverted to optional collection chambers, such as microfluidic collection chambers. Thus cell cytoplasm of unusual interest may be preserved for further analysis for further analysis by capillary electrophoresis, mass spectrometer, genetic analysis, or other analytic means.

Figure 6:
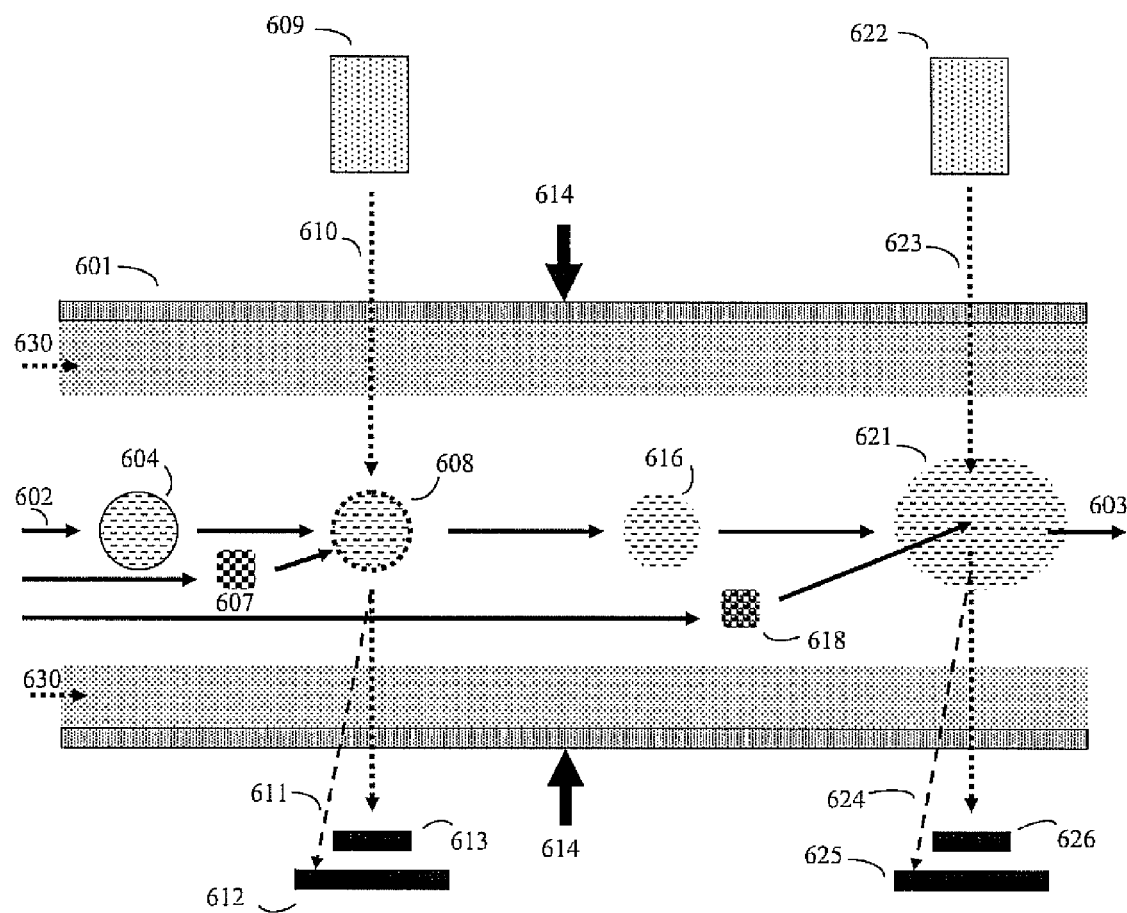
FIG. 6 shows a diagram of an embodiment of the higher functionality cell surface and cytoplasm analysis device.

FIG. 6 is yet another example of an embodiment of the invention that shows a more complex flow lysometer device that also employs sheath fluid methods to reduce problems of cells and cell debris clogging the device.

In contrast to the embodiment illustrated in FIG. 5, the embodiment in FIG. 6 may normally be constructed as one or more capillary channels etched or cut out of a larger substrate material, such as glass or plastic. This creates a hollow capillary channel bounded by walls (601) through which cell carrying fluid (602), normally consisting of buffered isotonic saline and other ingredients are introduced at an entry side. Unlike the first embodiment, however, this cell carrying fluid (602) is surrounded on at least one side by a sheath fluid (630). This sheath fluid may also consist of buffered isotonic saline with other ingredients, but will not contain cells or cell debris. This sheath fluid acts to prevent the capillary passages in the device from fouling, because the sheath fluid acts as a spacer, preventing cells and cell debris from contacting one or more walls of the capillary channel.

The cell-carrying-fluid normally exits at an exit side (603) and the fluid movement is often driven by electroosmotic force or a pump (not shown). The fluid contains a suspension of living cells (604). According to the previous embodiment, as these cells enter the capillary channel, they may pass through a narrow opening containing electrodes (not shown) which monitor the cell's size by detecting electrical current impedance changes, as described previously. Alternatively this electrode configuration may be omitted, and the cell size and structure may be determined by purely optical techniques.

As the cell passes through the capillary channel, an optional reagent port (not shown) may inject cell surface reagents. Often these cell surface reagents may consist of cell surface marker analysis reagents, such as fluorescent antibodies directed against cell surface markers of interest. However these cell surface reagents may also include surfactants or other agents (such as complement) to weaken the cell membrane, and may also include a tracking dye to monitor the fluid containing a cell of particular interest as it passes through the channel, or some other dye, such as calcein, intended to monitor the cell cytoplasm fragmentation field after the cell becomes lysed in a later step. Reagents (607) may also include cytoplasm analysis reagents intended to monitor the biochemical status of the cell's cytoplasm after the cell becomes lysed in a later step. In this example, reagents (607) are a fluorescent antibody against a cell surface marker of interest, and these antibodies bind to the surface of cell (604) creating an antibody labeled cell (608). Other possible reagents include cytoplasm marker dyes such as calcein.

In an alternative embodiment, cell surface reagents and or cytoplasm analysis reagents (607) are not be injected by a separate port, but rather may be mixed with the cell carrying fluid (602) before injection into the capillary device (201), and be carried along as part of fluid (602). This alternative embodiment allows for greater time for the reagents (antibodies, cytoplasm dyes, etc.) to interact with the cells, and also minimizes turbulence and potential obstructions in the capillary channel.

Prior to lysis, the status of cell (608) may be monitored by optical techniques. These techniques may include optical (often laser) light scattering and/or fluorescence monitoring techniques and/or automated video microscopy vision analysis techniques. Typically an optical light source, such as a laser (609), will direct a focused beam of light (610) at cell (608). Depending upon the analytic method contemplated, cell (608) will scatter some of this light, (611), and the magnitude and direction of this scatter will give information relating to cell contents and morphology, and this may be detected by photodetector (612). Often photodetector (612) will be protected by baffle (613) from direct exposure to un-scattered light from the light source. If a fluorescence measurement is contemplated, then photodetector (612) will normally employ wavelength-filtering devices (not shown) such as a bandpass filter, diffraction grating, or prism to ensure that the only light that is observed is wavelength shifted fluorescent light. If fluorescence observations are contemplated, often light source (609) will further control the wavelength range of emitted beam (610) by a emission bandpass filter or other filtering means (not shown).

Alternatively, the morphology of cell (608) may be monitored by video microscopy and an automated vision interpretation system, in which case detector (612) may be a microscope video detector. Depending upon the detection means chosen, the actual angle between the detector (612) and the illumination source (609) may vary. Although for simplicity, the drawing shows detector (612) located at a 180° angle from light source (609), in practice it will often be convenient to use a different angle, such as 90°, which will minimize interference from the direct beam (610).

After the optional pre-lytic optical analysis phase, the cell then moves into the lytic regions of the device (614). Here the cell may be lysed by one or more different means. The cell may pass into a lysing electrode (614) where the cell will be lysed by exposure to a high potential gradient. In this case, lysing zone (614) may be connected to an external electrical source via optional electrodes (not shown). Alternatively the lysing zone may expose the cells to a transient burst of ultrasonic energy, heat, light (e.g. a directed laser beam), or lytic chemical such as a surfactant such as SDS, in which case lysing zone (614) may be another reagent port.

For each embodiment illustrated in FIGS. 1-5, in another embodiment, computing devices and systems can be interfaced with cell electrodes or light analytical detectors (609), (610), (611), (612), (613) to make real-time decisions as to lyse or not lyse the cells based upon preset criteria. By combining such computing devices and systems with sheath flow techniques, the probability that the device will become clogged by cell debris may be reduced by many orders of magnitude.

After the cells are lysed in the lysing zone (614), the outer membrane of the cell will normally be in a non-intact state, exposing the contents of the cell's cytoplasm (616) to carrier buffer (602). As is shown, immediately after lysis, the cell's cytoplasm (debris field) will normally occupy a smaller area, which will tend to grow with time as diffusion and turbulence causes the cytoplasm to mix with the carrier buffer (602).

As the cell debris field continues to move along the capillary channel, it may pass a second reagent port (not shown) where one or more additional cell cytoplasm monitoring reagents may be added. These may be the ATP monitoring reagents luciferin and luciferase, or other reagents such as fluorescent or luminescent enzyme substrates, monoclonal antibodies, ionophores, molecular beacons, etc. as described previously. These reagents can be introduced either before or after lysis, and if necessary the length of the capillary channel may be extended (not shown in the drawing) to allow time for the reagents (618) to fully penetrate into the debris field (616) and react (619) with the contents of the cell cytoplasm.

In an alternative embodiment, reagents (618) will not be injected by a separate port, but rather may be mixed with the cell carrying fluid (602) before injection into the capillary device (601), and be carried along as part of fluid (602), as was previously discussed for the first embodiment device in FIGS. 1-4. This alternative embodiment simplifies device design, and may minimize turbulence and potential obstructions in the capillary channel. However, it may be unsuitable for a particular application if the cytoplasm analysis reagents are expensive or unstable.

After lysis, the cell debris may pass through an optional set of impedance or resistance monitoring electrodes (not shown). These will typically be used to confirm the extent of cell lysis, and will provide an important source of confirmation that cell (608) was, in fact, successfully lysed into cytoplasm debris field (616).

After the cell cytoplasm debris (621) has had time to adequately react with reagents (618), the debris field then passes through a cytoplasm analysis zone. If fluorescent reagents are contemplated, this zone may include an optical light source, such as a laser (622) and optional wavelength filtering devices such as a bandpass filter (not shown). If luminescent reagents are contemplated, then light source (622) is either not needed, or alternatively (and usually preferably) operated in a pulsed mode in which luminescence determinations are made during the period in which light source (622) is off. Generally operating light source (622) in a pulsed mode is preferred because this enables light source (622) to be used to allow the system to monitor the relative distribution of cytoplasm volume markers, such as calcein, in the debris field, and correct the cytoplasm reagent results for the distorting effects of variable debris field volume.

Here the beam of light (623) from light source (622) enters the debris field (621) where it may interact with cytoplasm volume markers such as calcein, or alternatively interact with fluorescent enzyme substrates, antibodies, ionophore reagents etc. Fluorescent (or luminescent) light emitted by the reagents (624) exits the debris field and is detected by photodetector (625). If fluorescence measurements are contemplated, photodetector (625) will usually have light filtering devices (not shown), such as a bandpass filter, diffraction grating, prism or other means to subtract the wavelengths of illumination beam (623) from the measurement.

Light scattering measurements may also be performed by light source (622), photodetector (625) and baffle (626) to monitor the status of the debris field. Alternately the status of the debris field may be monitored by video microscopy and automated image analysis techniques, in which case photodetector (25) will be a microscope video photodetector.

If desired, after this stage of the analysis, the exit fluid flow (603) containing cytoplasm debris may be diverted to optional collection chambers, such as microfluidic collection chambers. Thus cell cytoplasm of unusual interest may be preserved for further analysis for further analysis by capillary electrophoresis, mass spectrometer, genetic analysis, or other analytic means.

Figure 7:
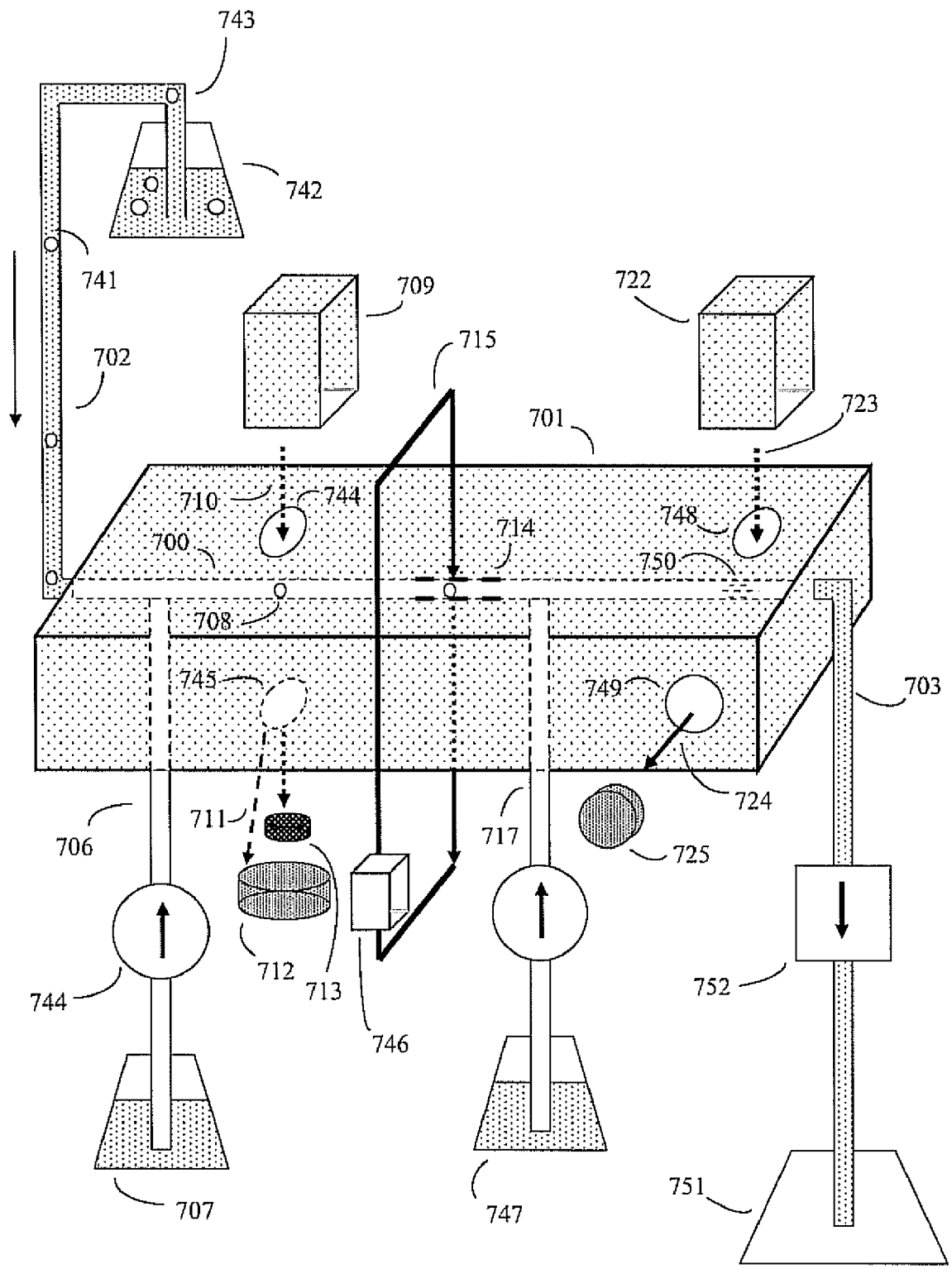
FIG. 7 shows some of the various fluid, device and electrical connections to the higher functionality cell surface and cytoplasm analysis device shown in FIG. 5.

FIG. 7 illustrates an example of fluid, analytical instrument, and electrical connections to the combination cell surface and cytoplasm analysis device shown in FIG. 5.

Here capillary channels (700) have been created in a substrate (701), which is usually glass or plastic. Cell carrier fluid (702) carries suspended living cells (741) into the capillary channels. Usually the cell carrier fluid and living cells are stored in a reservoir (742) connected to the device by tubing or other connection means (743).

In this diagram, to avoid cluttering the drawing with too many elements, the narrow opening containing conducting electrodes that monitor the cell sizes by electrical current impedance changes is not shown, but may be present if this option is desired. As per the earlier figures, often these reagents may consist of cell surface marker analysis reagents, such as fluorescent antibodies directed against cell surface markers of interest. However these reagents may also include surfactants or other agents (such as complement) to weaken the cell membrane, and may also include a tracking dye to monitor the fluid containing a cell of particular interest as it passes through the channel, or some other dye, such as calcein, intended to monitor the cell cytoplasm fragmentation field after the cell becomes lysed in a later step.

As per FIG. 5, prior to lysis, the status of the cells transiting the capillary channel (708) may be monitored by additional optical techniques. These techniques may include optical (often laser) light scattering and/or fluorescence monitoring techniques and/or automated video microscopy vision analysis techniques. Typically an optical light source, such as a laser (709), will direct a focused beam of light (710) at cell (708) often through an optical window (744) designed for this purpose. Depending upon the analytic method contemplated, cell (708) will scatter some of this light, (711), the magnitude and direction of this scatter will give information relating to cell contents and morphology, and this light may pass through an exit optical window (745) to photodetector (712). Often photodetector (712) will be protected by baffle (713) from direct exposure to un-scattered light from the light source.

Optionally fluorescence or automated video microscopy detection methods may be used. Depending upon the detection means chosen, the actual angle between the detector (712) and the illumination source (709) may vary. Although for simplicity, the drawing shows detector (712) located at an 180° angle from light source (709), in practice it will often be convenient to use a different angle, such as 90°, which will minimize interference from the direct beam (710).

As per FIG. 5, after the optional pre-lytic optical analysis phase, the cell then moves into the lytic zone of the device (714). Here the cell may be lysed by one or more different means. The cell may pass into a lysing electrode (714) where the cell will be lysed by exposure to a high electrical potential gradient. In this case, lysing zone (714) may be connected to an external electrical (746) source via optional electrical connections (715). Alternatively the lysing zone may expose the cells to a transient burst of ultrasonic energy, heat, light (e.g. a directed laser beam), or lytic chemical such as a surfactant such as SDS, in which case lysing zone (714) may another reagent port, another optical window, an ultrasonic horn port, heat pipe or other port.

After the cells are lysed in the lysing zone (714), the outer membrane of the cell will normally be in a non-intact state, exposing the contents of the cell's cytoplasm to the carrier buffer (702).

As the cell cytoplasm debris field continues to move along the capillary channel, it may pass a second reagent port (717) where one or more additional cytoplasm monitoring reagents may be added from reservoir (747). These may be the ATP monitoring reagents luciferin and luciferase, or other reagents such as fluorescent or luminescent enzyme substrates, monoclonal antibodies, ionophores, molecular beacons, etc. as described previously. Typically these reagents will be introduced immediately after lysis, and if necessary the length of the capillary channel may be extended (not shown in the drawing) to allow time for the reagents to fully penetrate into the debris field and react with the contents of the cell cytoplasm.

After lysis, the cell debris may pass through an optional set of impedance monitoring electrodes (not shown). As per FIG. 5, these will typically be used to confirm the extent of cell lysis, and will provide an important source of control (verification) information to the system.

After the cell cytoplasm debris has had time to adequately react with reagents, the debris field (750) then passes through a cytoplasm analysis zone. If fluorescent reagents are contemplated, this zone may include an optical light source, such as a laser (722) and optional bandpass filter or wavelength selection means (not shown). As per FIG. 1, if luminescent reagents are contemplated, then light source (722) is either not needed, or alternatively (and usually preferably) operated in a pulsed mode in which luminescence determinations are made during the period in which light source (722) is off.

As before, the beam of light (723) from light source (722) enters the cytoplasm debris field (750) in capillary channel (700) through optical window (748), where it may interact with cytoplasm volume markers such as calcein, or alternatively interact with fluorescent enzyme substrates, antibodies, ionophore reagents etc. previously introduced through ports (706) and (717). Fluorescent (or luminescent) light emitted by the reagents (724) exits the debris field through optical window (749), and is detected by photodetector (725). If fluorescence measurements are contemplated, photodetector (725) will usually have light filtering means (not shown), such as a bandpass filter, diffraction grating, prism or other means to subtract the wavelengths of illumination beam (723) from the measurement. Note that in FIG. 3, the exit window (749) and photodetector (725) are at a 90° angle from the incident light (723).

Light scattering measurements may also be performed by light source (722), photodetector (725) and a baffle (not shown) to monitor the status of the debris field (750). Alternately the status of the debris field (750) may be monitored by video microscopy and automated image analysis techniques, in which case photodetector (725) will be a microscope video photodetector.

If desired, after this stage of the analysis, the exit fluid flow (703) containing cytoplasm debris may be diverted a waste container (751) or to optional collection chambers, such as microfluidic collection chambers (not shown), gene analyzing chips, etc. Thus cell cytoplasm of unusual interest may be preserved for further analysis for further analysis by capillary electrophoresis, mass spectrometer, gene chip genetic analysis, or other analytic means.

Usually, the flow of reagents through the capillary device will be facilitated by an electroosmotic force or a downstream pump (752).

Here, the various electrically operated portions of the device, such as pumps (744), (752), light sources (709), (722), light detectors (712), (725), cell lysis means (746), (715) and other electrical means such as the electrodes (not shown) are preferably all connected to a computing means. This computing means will generally accept experimenter data as input (e.g. size and light scattering characteristics of the cell population of interest, how much reagent to add and when, cell lysis parameters) and other operating instructions and operate the device in a real-time manner based upon data from the device sensors, and the preset operational criteria. This computing means will usually also collect data from the sensors, analyze the data according to pre-set criteria, and present this data to the user.

Figure 8:
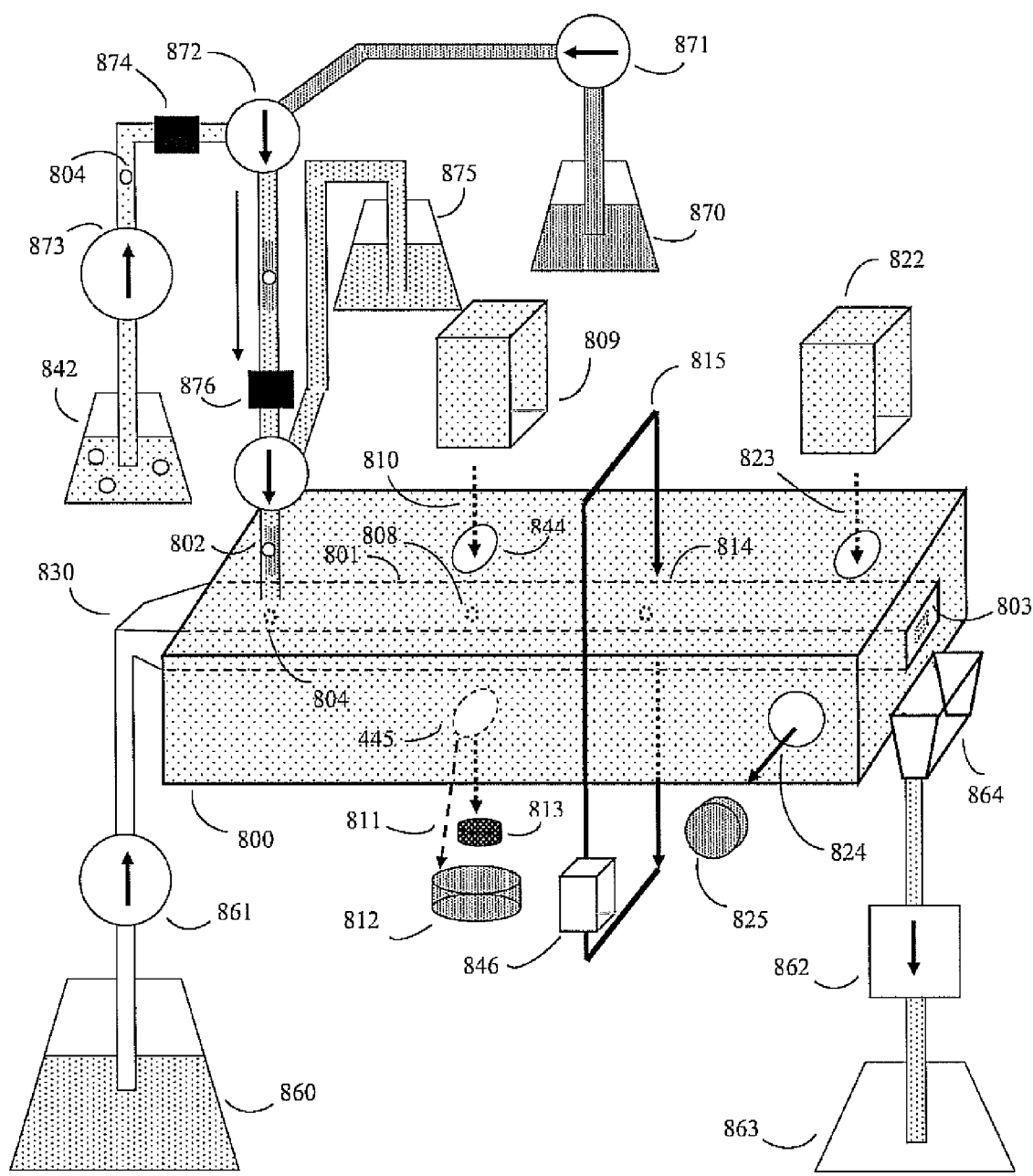
FIG. 8 shows some of the various fluid, device, and electrical connections to the higher functionality cell surface and cytoplasm analysis device shown in FIG. 6.

FIG. 8 shows an example of the fluid, analytical instrument, and electrical connections to the combination cell surface and morphology analysis and cell cytoplasm analysis device shown in FIG. 6.

As per the embodiment in FIG. 1-7, the device will normally be constructed as one or more capillary channels (801) etched or cut out of a larger substrate material (800), such as glass or plastic. This creates a hollow capillary channel bounded by walls (801) through which cell carrying fluid (802), normally consisting of buffered isotonic saline and other ingredients pumped out of a reservoir containing a suspension of living intact cells (842) is introduced at an entry side. Unlike the FIGS. 1-5 and 7 embodiments, however, this cell carrying fluid (802) is surrounded on at least one side by sheath fluid (430) that is typically introduced to the capillary channel ahead of (before) the cell carrying fluid (802). Often sheath fluid (830) will be pumped into the device from a sheath fluid reservoir (860) via a pump (861).

As per FIG. 6, this sheath fluid may also consist of buffered isotonic saline with other ingredients, but will not contain cells or cell debris. This sheath fluid acts to prevent the capillary passages in the device from fouling by acting as a spacer that prevents cells and cell debris from contacting at least one wall of the capillary channel.

The cell carrying fluid normally exits at an exit side (803) and the fluid movement is often driven by a pump (862) connected to the exit side (803), which pumps the fluid into a waste container (863) or alternatively into other devices for further testing and or use. For artistic reasons, in order to better show the inner structure of the cell transport fluid and the sheath fluid in the capillary channels, the end of the device is not connected to the pump, but rather is shown dumping the excess fluid into a collection trough (864) that is in turn connected to a pump. In the actual structure, this gap and collection trough (864) will normally not occur.

The cell carrier fluid contains a suspension of living cells (804). As per earlier embodiments, as these cells enter the capillary channel, they may pass through a narrow opening containing electrodes which monitor the cell's size by detecting electrical current impedance changes, as described previously (not shown). Alternatively this electrode configuration may be omitted, and the cell size and structure may be determined by purely optical techniques.

As the cell passes through the capillary channel, an optional reagent port (not shown) may inject cell surface reagents, previously described in the earlier Figures. This drawing shows an alternative embodiment however, which is more similar to FIGS. 1-4. In this embodiment, both the cell surface reagents and the cytoplasm analysis reagents are injected along with the cell and the cell carrier fluid through the same port. This particular embodiment can be advantageous when sheath fluids are used, because all reagents and cells are introduced through a single port, minimizing disruption of the sheath fluid, and thus minimizing the chances that the device will be fouled by cells or cell debris.

In this particular configuration, cell surface reagents stored in cell surface reagent reservoirs (870) are pumped in via pumps (871) (872) to mix with the cells (804) and cell carrier fluid (802) before entering the capillary channel. However electroosmotic means or alternative pumping means may also be used.

Often, cell surface reagents may be expensive, and it may be desirable to control costs by only using them on appropriate cells. To do this, cells from cell reservoir (842) may be pumped through valve (873) past detector (874). Detector (874) may be an electrode based cell impedance detector or light scattering detector. Depending upon the output from detector (874), cell surface reagents from reservoir (870) may or may not be pumped through pumps and valves (871) and (872) to mix with the cells. For example, the detector (874) and pumps and valves (871), (872), (873) may be controlled by a microprocessor (not shown) that is programmed to only administer reagent (870) to cells of a certain size.

After the cells (804) mix with reagent from cell surface reagent reservoir (870), the cells and cell surface reagent may also pass through a second detector (876) before entering the capillary device (800). As an example, second detector (876) may be another electrical impedance or resistance detector, or alternatively may be a cell surface fluorescence detector. These will usually be hooked up to computing devices and systems such as a microprocessor (not shown). Depending upon the results from this second analysis, cell cytoplasm analysis reagents from container (875) may or may not be added to the cell before it enters the reaction chamber. This alternative embodiment allows for greater time for the reagents (antibodies, cytoplasm dyes, etc.) to interact with the cells, and also minimizes turbulence and potential obstructions in the capillary channel.

As before, prior to lysis, the status of cell (808) may be monitored by additional optical techniques. These techniques may include optical (often laser) light scattering and/or fluorescence monitoring techniques and/or automated video microscopy vision analysis techniques. Typically an optical light source, such as a laser (809), will direct a focused beam of light (810) through optical window (844) at cell (808). Depending upon the analytic method contemplated, cell (808) will scatter some of this light, (811), and the magnitude and direction of this scatter will give information relating to cell contents and morphology, and this will pass through optical window (845) to be detected by photodetector (812). Often photodetector (812) will be protected by baffle (813) from direct exposure to un-scattered light from the light source.

As before, if a fluorescence measurement is contemplated, then photodetector (812) will normally employ wavelength-filtering devices (not shown) such as a bandpass filter, diffraction grating or prism to ensure that the only light that is observed is wavelength shifted fluorescent light. If fluorescence observations are contemplated, often light source (809) will further control the wavelength range of emitted beam (810) by a emission bandpass filter or other filtering devices (not shown). Alternatively, the morphology of cell (808) may be monitored by video microscopy and an automated vision interpretation system, in which case detector (812) may be a microscope video detector. Depending upon the detection means chosen, the actual angle between the detector (812) and the illumination source (809) may vary. Although for simplicity, the drawing shows detector (812) located at an 180° angle from light source (809), in practice it will often be convenient to use a different angle, such as 90°, which will minimize interference from the direct beam (810).

After the optional pre-lytic optical analysis phase, the cell then moves into the lytic regions of the device (814). Here, as before, the cell may be lysed by one or more different methods. The cell may pass into a lysing electrode (814) where the cell will be lysed by exposure to a high potential gradient. In this case, lysing zone (814) may be connected to an external electrical source (846) via optional electrodes (815). Alternatively the lysing zone may expose the cells to a transient burst of ultrasonic energy, heat, light (e.g. a directed laser beam), or lytic chemical such as a surfactant such as SDS, in which case lysing zone (814) may be another reagent port, optical window, ultrasonic horn port, heat pipe port or other type of port.

After the cells are lysed in the lysing zone (814), the outer membrane of the cell will normally be in a non-intact state, exposing the contents of the cell's cytoplasm to carrier buffer (802).

As the cell debris field continues to move along the capillary channel, it may pass a second reagent port (not shown) where one or more additional cytoplasm monitoring reagents may be added. As previously discussed however, FIG. 8 shows an alternative embodiment, similar to that used in the first embodiment device previously described in FIGS. 1-4, in which both the cell surface analysis reagents (870) and cell cytoplasm analysis reagents (875) were mixed with the cells (804), (842) prior to entering the capillary device (801). As previously discussed, this alternative embodiment may use more reagents, but simplifies device design, and minimizes turbulence and potential obstructions in the capillary channel.

After lysis, the cell debris may pass through an optional set of impedance monitoring electrodes (not shown). These will typically be used to confirm the extent of cell lysis, and will provide an important source of control (verification) information to the system.

As before, after the cell cytoplasm debris has had time to adequately react with reagents, the debris field then passes through a cytoplasm analysis zone. If fluorescent reagents are contemplated, this zone may include an optical light source, such as a laser (822) and optional wavelength filtering devices such as a bandpass filter (not shown). If luminescent reagents are contemplated, then light source (822) is either not needed, or alternatively (and usually preferably) operated in a pulsed mode in which luminescence determinations are made during the period in which light source (822) is off. Generally operating light source (822) in a pulsed mode is preferred because this enables light source (822) to be used to allow the system to monitor the relative distribution of cytoplasm volume markers, such as calcein, in the debris field, and correct the cytoplasm reagent results for the distorting effects of variable debris field volume.

As before, the beam of light (823) from light source (822) enters the cell cytoplasm debris field (not shown) where it may interact with cytoplasm volume markers such as calcein, or alternatively interact with fluorescent enzyme substrates, antibodies, ionosphere reagents etc. Fluorescent (or luminescent) light emitted by the reagents (824) exits the debris field and is detected by photodetector (825). If fluorescence measurements are contemplated, photodetector (825) will usually have light filtering devices (not shown), such as a bandpass filter, diffraction grating, prism or other devices to subtract the wavelengths of illumination beam (823) from the measurement.

Light scattering measurements may also be performed by light source (822), photodetector (825) and baffle (not shown) to monitor the status of the debris field. Alternately the status of the debris field may be monitored by video microscopy and automated image analysis techniques, in which case photodetector (825) will be a microscope video photodetector.

As before, after this stage of the analysis, the exit fluid flow (803) containing cytoplasm debris may be diverted to optional collection chambers, such as microfluidic collection chambers. Thus cell cytoplasm of unusual interest may be preserved for further analysis by capillary electrophoresis, mass spectrometer, genetic analysis, or other analytic means.

As per FIG. 7, the various electrically operated portions of the device, such as pumps and valves (861), (862), (873), (871), (872), (873), cell electrodes or light scattering detectors (874), (876), light sources (809), (822), light detectors (812), (825), cell lyser (846), (815) and other electrical sensors such as the electrodes (not shown) are preferably all connected to computing devices and/or systems. This computing device and or system will generally accept experimenter data as input (e.g. size and light scattering characteristics of the cell population of interest, how much reagent to add and when, cell lysis parameters) and other operating instructions and operate the device in a real-time manner based upon data from the device sensors, and the preset operational criteria. This computing device and/or systems will usually also collect data from the sensors, analyze the data according to pre-set criteria, and present this data to the user.

Figure 9:
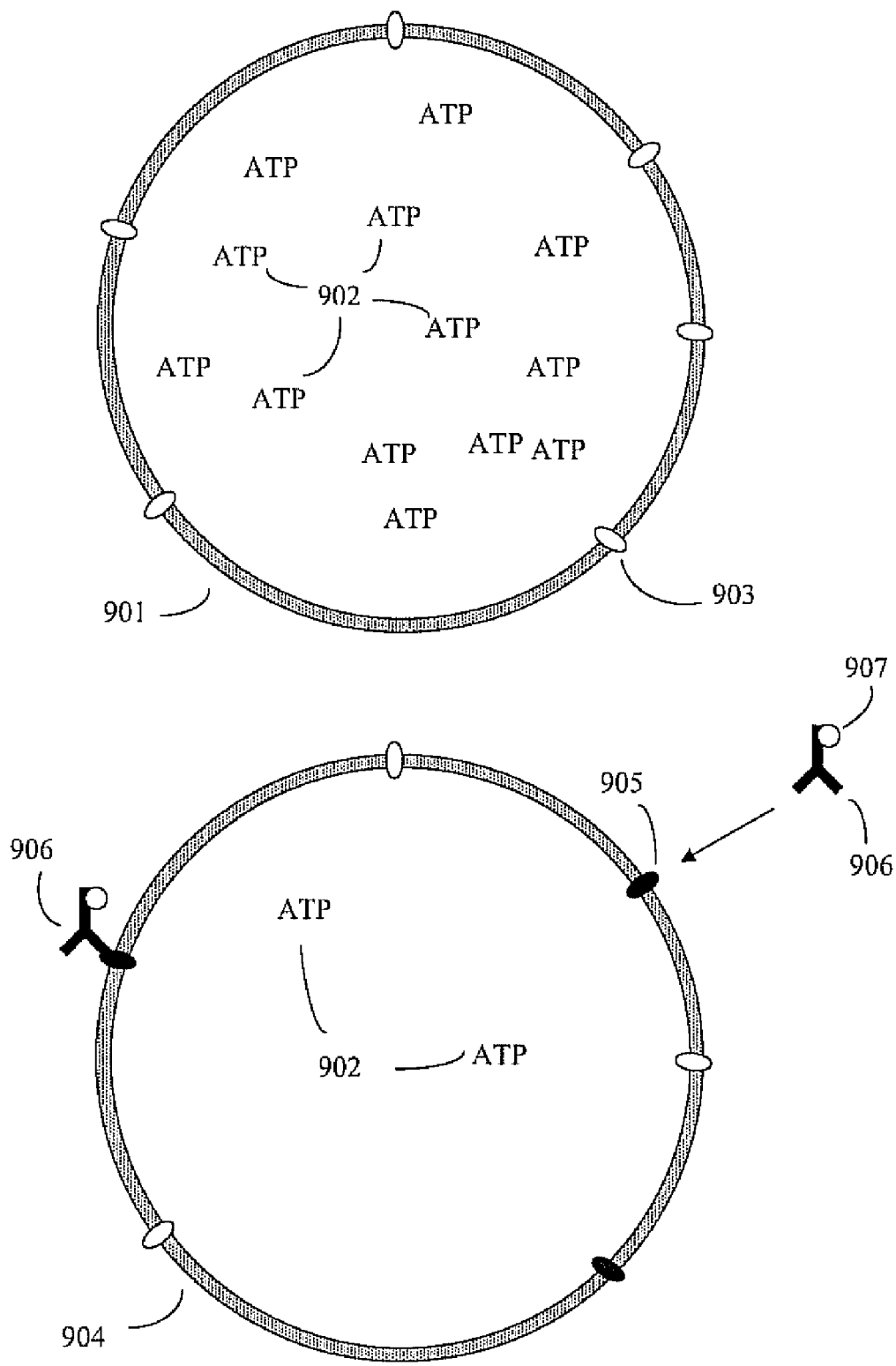
FIG. 9 gives an example of the correlation between the cell surface molecules and the cell cytoplasm ATP concentration for a hypothetical cell population containing two types of cells.

FIG. 9 shows a diagram showing an example of the correlation between cell surface molecules and internal cell cytoplasm biochemistry for two different cell types.

The first cell type, (901), has high internal ATP levels (902) and a cell surface antigen type "A" (903). The second cell type, (904), has low internal ATP levels (902) and a cell surface antigen type "B" (905). The two cell types otherwise have similar diameters and volumes. When exposed to a cell-surface-analysis reagent comprising a fluorescent anti-B antibody (906) with a fluorescent label (907), the anti-B antibody reacts with cell surface antigen "B" but not "A", and the fluorescent anti-B antibody will primarily bind to the second cell type (904).

Alternatively, the two cell types may represent red cells of two different sizes, such as a small red cell (901) where the high ATP levels power the cell's cytoskeleton and ionic pumps and prevent the cell from swelling. Here 904 would represent an older or damaged red cell with lower ATP levels that has started to swell up in size because it does not have sufficient ATP to maintain its cytoskeletal system and ionic pumps.

Figure 10:
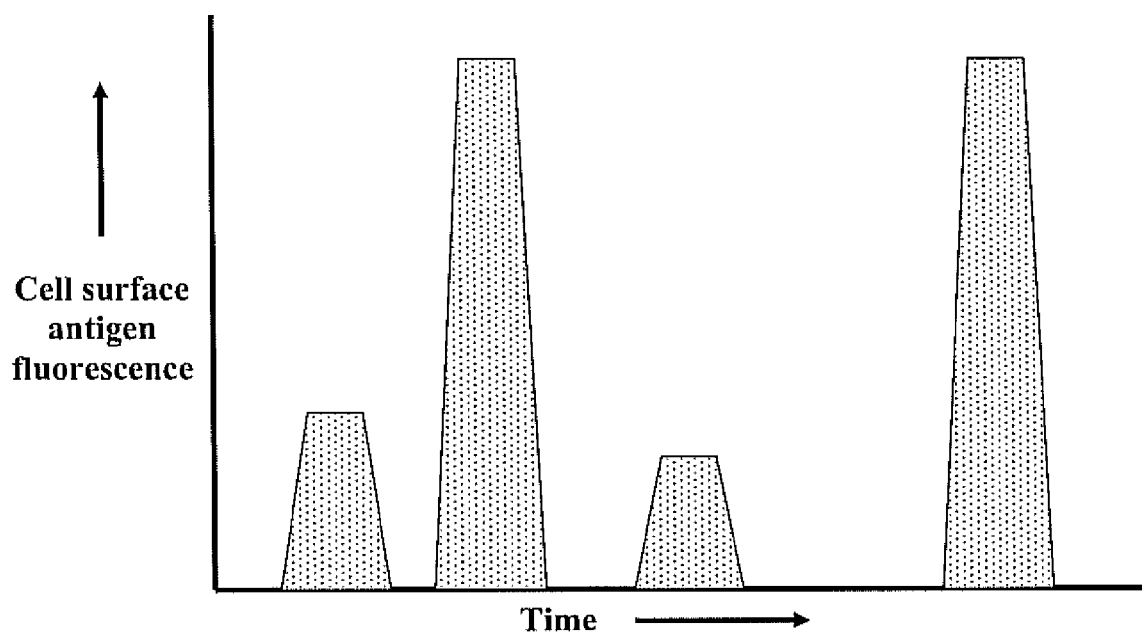
FIG. 10 shows an example of the cell surface molecule data that would be output by the combination cell surface and cytoplasm analysis device upon analyzing the cell population shown in FIG. 9.

FIG. 10 shows an example of the type of cell surface morphology or cell surface molecule data that can be obtained using this device.

In this example, assume that a population of four cells, consisting of two cells with low levels of cell surface antigen "B", and two cells with high levels of cell surface antigen "B" (previously shown in FIG. 9) have been analyzed in the device. The output from the cell surface antigen fluorescence detector shows detects this, but tells us nothing about ATP levels. If the cellular ATP levels were analyzed by classical techniques—that is grinding up all the cells, the differences between cell ATP levels would average out would be missed.

Figure 11:
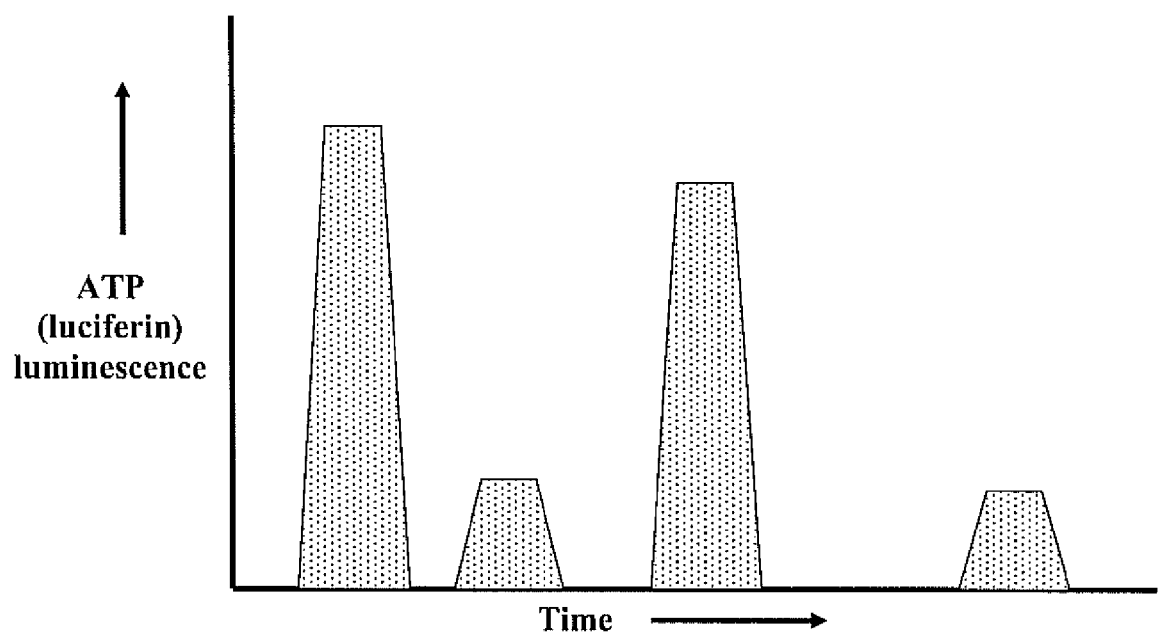
FIG. 11 shows an example of the cell cytoplasm ATP concentration data that would be output by the combination cell surface and cytoplasm analysis device upon analyzing the cell population shown in FIG. 9.

FIG. 11 shows an example of the type of cytoplasmic biochemistry results (here ATP levels are shown) that can be obtained using the device.

In this example, assume that the same population of four cells from FIGS. 9 and 10 were also analyzed for cell ATP levels. Here the ATP luciferin luminescence outputs for the four cells are shown. As can be seen, two cells have low levels of ATP, and two cells have high levels of ATP. To correlate these results with the cell surface antigen properties of the cells, data analysis is required, which will ideally be performed by computational means attached or connected to the device.

Figure 12:
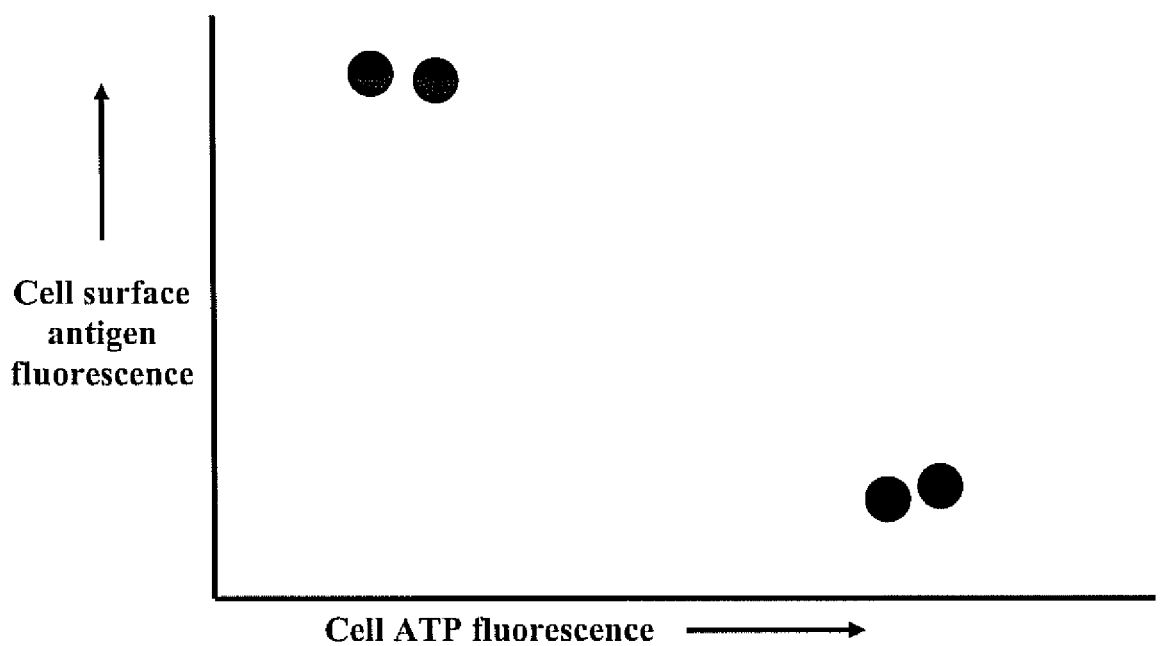
FIG. 12 shows an example of how a processor attached to the combination cell surface and cytoplasm analysis device might combine the data from FIGS. 10 and 11 to produce a graphical report of the state of the cell population that would allow researchers or clinicians to deduce that the overall state of the cell population being analyzed is as shown in FIG. 9.

FIG. 12 shows an example of the type of data that can be produced by suitable computational means attached to the device. Here the cell morphology or cell surface molecule data is plotted versus the cell cytoplasm biochemistry data, and the two data types, when combined, allow the experimenter to see that the high cell surface antigen "B" cells have low ATP levels, and the low cell surface antigen "B" cells have high ATP levels. This allows the experimenter to determine that the cell population under investigation has the characteristics of the cells shown in FIG. 9.

The invention may also involve a number of functions to be performed by a computer devices and or systems such as a computer processor, which may be as simple as combinatorial logic, or may include more complex devices such as a microprocessor. The microprocessor may be a specialized or dedicated microprocessor that is configured to perform particular tasks by executing machine-readable software code that defines the particular tasks. The microprocessor may also be configured to operate and communicate with other devices such as direct memory access modules, memory storage devices, Internet related hardware, and other devices that relate to the transmission of data in accordance with the invention. The software code may be configured using software formats such as assembly, Java, C++, XML (Extensible Mark-up Language) and other languages that may be used to define functions that relate to operations of devices required to carry out the functional operations related to the invention. The code may be written in different forms and styles, many of which are known to those skilled in the art. Different code formats, code configurations, styles and forms of software programs and other means of configuring code to define the operations of a microprocessor in accordance with the invention will not depart from the spirit and scope of the invention.

Within the different types of computers, such as standalone microprocessors, microprocessor arrays, and computer servers, that utilize the invention, there exist different types of memory devices for storing and retrieving information while performing functions according to the invention. Cache memory devices are often included in such computers for use by the central processing unit as a convenient storage location for information that is frequently stored and retrieved. Similarly, a persistent memory is also frequently used with such computers for maintaining information that is frequently retrieved by a central processing unit, but that is not often altered within the persistent memory, unlike the cache memory. Main memory is also usually included for storing and retrieving larger amounts of information such as data and software applications configured to perform functions according to the invention when executed by the central processing unit. These memory devices may be configured as random access memory (RAM), static random access memory (SRAM), dynamic random access memory (DRAM), flash memory, and other memory storage devices that may be accessed by a central processing unit to store and retrieve information. The invention is not limited to any particular type of memory device, or any commonly used protocol for storing and retrieving information to and from these memory devices respectively.

In addition to playing a major role in analyzing data produced by the device, the computer processor may also run the lysometer in various modes according to criteria set by the user. As an example, the user may input criteria into the computer that directs the computer to only lyse cells that meet certain preset criteria, and not to lyse other types of cells. Alternatively the user may also instruct the computer to dynamically assess the success of attempted cell lysis, and change lysis parameters (e.g. increase lysis voltage) if data suggest that cells are not being lysed with high enough efficiency. The computer or processor may also be directed to increase or decrease flow rates according to cell density (e.g. increase flow rates with when the number of cells per ml is smaller, and decrease flow rates when the number of cells per ml is larger). The computer or processor may also be directed to divert cells or cell debris fields to different chambers of the microfluidic device depending upon the cell surface or cell interior data. For example, a cell debris field containing a marker of particular interest could be diverted to a collection region of the microfluidic device for more detailed analysis.

Microchannels may be fabricated according to the design shown in FIGS. 1, 2, and 3. The device is essentially a silicon-wafer glass-wafer sandwich. The silicon wafer PolyDiMethylSiloxane (PDMS) portion is patterned by standard micro-molding techniques using 3.0 μm-thick negative photoresist (SU-8 2002). Electrodes may be produced on the glass portion of the device by sputtering Cr and Au layers on the glass wafers at the thickness of 200 Å and 2000 Å, respectively, and their final electrode geometry may then be patterned. Finally, the PDMS micro channel and the glass substrate may be bonded together using a high frequency generator, BD-10AS (Electro-Technic Products, INC), forming the microchannel portion of the lysometer.

Cell passage through the various lysometer passageways may be detected by electrically sensing cell passage through the electrodes 105, 106, which may be gold electrodes, and this passage may also be confirmed by video microscopy. Cell lysis may be induced by a 1.2 kV/CM electrical field across the lysis region (212), and successful lysis can also be confirmed by video microscopy. ATP may be detected using a commercially available ATP luciferin/luciferase detection kit (SIGMA, St. Louis). The lysometer channel may be filled with this luciferin/luciferase ATP detection mixture, and the light produced when ATP is released into this detection mixture by lysed cells may be detected and quantitated by video microscopy (note that to measure the mixture the light generated in this reaction, the light of the microscope condenser should be turned off). In this type of detection method, the microscope's digital camera can be used as the photon detector, and video microscopy allows the photons collected in time by each pixel of the camera to be analyzed. The system may be calibrated by first adding different amounts of ATP, and the response of the system determined. Typically, when the camera is a Photometric FX camera and the microscope is an Olympus IX 70 microscope, the sensitivity of this system is capable of detecting the ATP contained in a single red blood cell.

The system may be further tested and calibrated by using mixtures of human and murine (mouse) red blood cells, which differ significantly in size, and thus can be distinguished from each other by video microscopy. The cells can then be stored in either an ATP maintaining buffer (ATP+) (10 mM Hepes, 150 mM NaCl, 5 mM KCl, 5 mM glucose, 10 mM Inosine, 5 mM Pyruvate and 0.2 mM $Na_2HPO_4$) or an ATP depletion buffer (ATP−) (10 mM Hepes, 130 mM NaCl, 2.7 mM KCl, 1 mM EGTA, 10 mM Inosine, 6 mM iodoacetamide, 5 mM tetrathionate).

After incubation (typically 30 minutes to deplete ATP levels to 10% of the original level) in the ATP-buffer, the cells can then be resuspended in 100 mM phosphate buffered saline, pH 7.4, 310 mosmol, prior to analysis.

Cells may optionally be surface labeled with 10 nM biotinylated di-annexin followed by phycoerythrin-conjugated strepavidin and analyzed by flowcytometry.

The cell populations may then be introduced to the device, and flow generated by either syringe pumps or electro-osmotic flow. When the injected RBCs pass through the electrical detection zone (between two electrodes), electrical pulses are generated due to a change in conductivity (resistance). The electrical pulses can also be used to synchronize the detection in the component-sensing part. This flow rate-dependent synchronization can be used to trigger the component-sensing, thus reducing the measurement noise. The voltage in the lysis region disrupts the RBC, the released cytosolic components mix with the chemiluminescent agent in the channel, and the light is detected by video microscopy. Typical operating parameters are: applied voltage: 33.8V, flow velocity at the component sensing part: ~160 um/s, e-field at the sensing part: 0.3 kV/cm, e-field at the lysis part: 1.2 kV/cm).

The flow lysometer chip may be mounted on the stage of a high performance microscope (Olympus IX 70), equipped with a sensitive digital camera (Coolsnap fx, Photometrics). The microscope enables not only the chemiluminescence light sensing but also the direct monitoring of cell passage and lysis in the micro channel. After the verification of basic operation, this microscope may be replaced by a sensitive photon-detector, such as a photo multiplier tube (PMT). For experimental verification, a mixture of cells in which part of the population is ATP depleted may be prepared from human and murine RBC as previously described. The difference in size between human and murine cells (volumes of approximately 90 and 40 fl respectively) provides a different coulter pulse in the cell counting part of the device. Samples of mixtures of normal and ATP depleted cells can be pumped through the device in the presence of the ATP measuring buffer. Cell lysis leads to luminescence and is measured by the photon detection system.

Fluorescently labeled cells can be detected before they enter the lysometer by use of a Guava EasyCyte (Guava Inc, Hayward, Calif.). The Guava EasyCyte is a 3 color flowcytometer that does not use sheath fluid, but rather uses a syringe pump to pull a sample though the capillary flow cell. Samples may pass through the EasyCyte, their surface fluorescent monitored, and the cell may then pass into the lysometer. The electronics and software of the EasyCyte may be altered to facilitate data collection and synchronization of signals between the EasyCyte and the lysometer. For experimental test purposes, either the ATP depleted cells or the normal cells (but not both) may be fluorescently labeled. This way the correlation between the known ATP+ cells (as verified by their fluorescent surface label) and their measured ATP levels (as determined by the lysometer) may be determined, and the proper functioning of the overall device verified.

The apparatus and method include a method and apparatus for analyzing cells using a microfluidic flow lysometer device. Although this embodiment is described and illustrated in the context of devices, systems and related methods of analyzing cells using methods devices and systems described herein, the scope of the invention extends to other applications where such functions are useful. Furthermore, while the foregoing description has been with reference to particular embodiments of the invention, it will be appreciated that these are only illustrative of the invention and that changes may be made to those embodiments without departing from the principles of the invention or the spirit and scope of the invention as defined by the appended claims and their equivalents.

The invention claimed is:

1. A method for performing a population analysis on a plurality of cells while in transit in at least one dynamic microfluidic pathway, the method comprising:
    providing a population of cells having cell surface indicia;
    transmitting the population of cells through the microfluidic pathway;
    analyzing the cell surface indicia to obtain a first set of data corresponding to each cell of the population of cells;
    utilizing a processor to compare the first set of data with at least one preset user criteria to identify at least one cell satisfying the preset user criteria;
    utilizing the processor to control operation of a cell lyser to selectively lyse the at least one cell while it transits a microfluidic pathway to produce cell debris that exposes cell interior indicia, wherein cells that do not satisfy the preset user criteria are not lysed; and
    analyzing the cell interior indicia for at least one of a molecule and a cellular component.

2. The method according to claim 1, in which the cell surface indicia are selected from the group consisting of cell size, cell shape, cell morphology, cell narrow angle light scattering, cell wide angle light scattering, cell electrical characteristics, cell surface membrane molecules, and cell surface markers.

3. The method according to claim 1, in which the cell interior indicia are selected from the group consisting of cell cytoplasmic-side membrane molecules, cell cytoplasm molecules, cell nuclear membrane molecules, cell nuclear molecules, DNA, RNA, cell interior proteins, cell interior lipids, cell interior carbohydrates, cell interior cofactors, cell interior ions, cell interior ATP, cell organelles, and cell organelle molecules.

4. The method according to claim 1, further comprising: combining data from at least one of the cell's surface indicia and data from at least one of the cell's interior indicia from a plurality of the at least one cell to produce a population analysis of the cells.

5. The method according to claim 1, wherein at least one of the cell surface indicia and the cell interior indicia is analyzed while the at least one cell transits the microfluidic pathway, and wherein the at least one cell is alive as it enters the microfluidic pathway.

6. A method for performing a population analysis on a plurality of cells, in which the plurality of cells is analyzed on an individual cell-by-cell basis for specific cell surface markers or specific morphological characteristics, and the individual data obtained on a cell-by-cell basis then assembled into a statistical analysis of the population of cells, the method comprising:
providing a population of cells;
causing the population of cells to travel through a microfluidic pathway;
analyzing the population of cells to obtain a first set of data corresponding to each cell of the population of cells, the first set of data describing at least one of cell surface markers and specific morphological characteristics identify at least one cell having predetermined morphological characteristics;
utilizing a processor to compare the first set of data with at least one preset user criteria to identify at least one cell satisfying the preset user criteria;
utilizing the processor to control operation of a cell lyser to selectively lyse the at least one cell; and
analyzing the at least one lysed cell.

7. The method of claim 6, wherein the step of lysing the at least one cell is selected from the group consisting of electrical lysing, chemical lysing, osmotic lysing, ultrasonic lysing, laser lysing, and heat lysing methods.

8. The method of claim 6, in which the step of analyzing the population of cells to identify at least one cell having predetermined morphological characteristics is selected from the group consisting of electrode-based electronic measuring methods, light scattering methods, fluorescence detection methods, luminescence detection methods, light absorbance detection methods, automated video microscopy, and vision recognition methods.

9. The method of claim 6, wherein the step of causing the population of cells to travel through a microfluidic pathway utilizes a moving fluid stream either with or without a sheath fluid, and is capable of transporting the cells through at least part of the microfluidic pathway in an intact state; and
wherein the step of lysing the at least one cell occurs while the at least one cell is transiting through the microfluidic pathway.

10. The method of claim 6, in which the step of analyzing the at least one lysed cell is a biochemical analysis method selected from the group consisting of fluorescent ion indicator methods, luminescent ion indicator methods, chromogenic enzyme substrate methods, fluorescent enzyme substrate methods, luminescent enzyme substrate methods, fluorescent antibody methods, enzyme labeled antibody methods, luminescent antibody methods, molecular beacon methods, genetic analysis device methods, fluorescent nucleic acids methods, and luminescent nucleic acid methods.

11. The method of claim 6, in which the method of analyzing the at least one lysed cell further comprises compensating for the distorting effects caused by the variable volume of the cell lysis field by:
incorporating a fluorescent or luminescent tracking dye into the cells before lysis;
and
monitoring the fluorescence or luminescence distribution of the tracking dye when it is released from the at least one lysed cell.

12. The method of claim 6, further comprising using a processor to analyze the population of cells to identify at least one cell having predetermined morphological characteristics.

13. The method of claim 6, wherein analyzing the population of cells to identify at least one cell having predetermined morphological characteristics comprises using a processor to analyze at least one of cell surface markers and cell morphological characteristics, wherein the analysis comprises:
obtaining a first set of data pertaining to at least one of the cell surface markers and the cell morphological characteristics of the at least one cell;
biochemically analyzing at least one of the cytoplasm and nuclear debris field of the at least one cell;
obtaining a second set of data pertaining to at least one of the cytoplasm and the nuclear debris field; and
correlating the first set of data and the second set of data according to user determined criteria, the results of which are at least one of stored and transmitted.

14. A device for correlating an individual cell's cell surface markers or cell morphological characteristics with one or more molecules present in the cell cytoplasm or nucleus of the individual cells; the device being capable of operating on a plurality of individual cells selected from a population of cells;
comprising:
one or more microfluidic pathways containing a moving fluid stream capable of transporting the individual cells through at least a portion of the microfludic pathways in an intact state;
at least one transit analyzer configured to analyze the cell surface markers or the cell morphological characteristics of the individual cells while the cells are transiting the microfluidic pathways in an intact state;
a cell lyser configured to lyse the individual cells while the cells are transiting the microfluidic pathways to expose a cytoplasmic and nuclear debris field; and
at least one biochemistry analyzer configured to biochemically analyze the cytoplasmic or nuclear debris field of the lysed cells for the one or more molecules present in the cell cytoplasm or the nucleus of the individual cell.

15. The device of claim 14, in which the cell lyser is selected from the group consisting of electrical lysers, chemical lysers, osmotic lysers, ultrasonic lysers, laser lysers, and heat lysers.

16. The device of claim 14, in which the transit analyzer used to analyze the cell surface markers or the cell morphological characteristics is selected from the group consisting of electrode based electronic sensors, light scattering sensors, color detection sensors, fluorescence detection sensors, luminescence detection sensors, and automated video microscopy vision recognition sensors.

17. The device of claim 14, in which the microfluidic pathways of the device carry the cells in a moving fluid stream that is protected from contact with at least one wall of the microfluidic pathways by a sheath fluid.

18. The device of claim 14, in which the biochemistry analyzer configured to analyze the debris field of the lysed cells utilizes biochemical reagents selected from the group consisting of fluorescent ion indicators, luminescent ion indicators, chromogenic enzyme substrates, fluorescent enzyme substrates, luminescent enzyme substrates, fluorescent antibodies, enzyme labeled antibodies, luminescent antibodies, molecular beacons, genetic analysis devices, fluorescent nucleic acids, and luminescent nucleic acids.

19. The device of claim 14, in which the biochemistry analyzer corrects for the distorting effects caused by the variable volume of the cell lysis field by also monitoring the fluorescence or luminescence distribution of a cell cytoplasm tracking dye that is released upon cell lysis.

20. The device of claim 14, further containing a processor connected to the transit analyzer and the cell lyser;
   in which the processor use data obtained from the transit analyzer to control the operation of the cell lyser.

21. The device of claim 14, further containing a processor connected to the transit analyzer;
   wherein the processor obtains a first set of data pertaining to the cell surface markers or the cell morphological characteristics of the individual cells;
   the processor also being connected to the biochemistry analyzer to biochemically analyze the cytoplasm or nuclear debris field of the lysed cells;
   wherein the processor obtains a second set of data pertaining to the one or more molecules present in the cell cytoplasm or the nucleus of the individual cells;
   in which the processor correlates the first set of data and the second set of data according to user determined criteria and store or transmit the correlated data.

22. A device for correlating an individual cell's cell surface markers or cell morphological characteristics with one or more molecules present in the cell cytoplasm or nucleus of the individual cells;
   the device being capable of operating on a plurality of individual cells selected from a population of cells;
   the device comprising;
   one or more microfluidic pathways;
   the microfluidic pathways containing a moving fluid stream capable of transporting the individual cells through at least a portion of the microfludic pathways in an intact state;
   a transit analyzer to analyze the cell surface markers or the cell morphological characteristics of the individual cells while the cells are transiting the microfluidic pathways in an intact state;
   a cell lyser to lyse the individual cells while the cells are transiting the microfluidic pathways;
   a biochemistry analyzer to biochemically analyze the cytoplasmic or nuclear debris field of the lysed cells for the one or more molecules present in the cell cytoplasm or the nucleus of the individual cell; and
   a processor configured to process data collected from the transit analyzer to analyze the cell surface markers or the cell morphological characteristics to operate either the cell lyser or the cell biochemistry analyzer.

23. The device of claim 22, wherein the processor is configured to obtain a first set of data pertaining to the cell surface markers or the cell morphological characteristics of the individual cells;
   wherein the processor is configured to obtain a second set of data pertaining to the one or more molecules present in the cell cytoplasm or the nucleus of the individual cells;
   in which the processor is configured to correlate the first set of data and the second set of data according to user determined criteria and store or transmit the correlated data.

24. The device of claim 22, wherein the processor is configured to obtain a first set of data pertaining to the cell surface markers or the cell morphological characteristics of the individual cells, compare the first set of data with one or more preset user criteria, and vary the operation of the cell lyser to lyse the individual cells;
   wherein cells that meet one or more preset user criteria are lysed, and wherein cells that fail to meet one or more preset user criteria are not lysed.

25. The device of claim 22, wherein the processor is configured to obtain a first set of data pertaining to the cell surface markers or the cell morphological characteristics of the individual cells, or wherein the processor is configured to obtain a second set of data pertaining to the one or more molecules present in the cell cytoplasm or the nucleus of the individual cells;
   and wherein processor is configured to compare said first data or said second data with one or more preset user criteria, and alter the flow speed or flow direction of said cells or said cell debris through said microfluidic pathways when said first set of data or said second set of data meet one or more of said preset user criteria.

* * * * *